US011382704B2

(12) United States Patent
Overmyer et al.

(10) Patent No.: US 11,382,704 B2
(45) Date of Patent: Jul. 12, 2022

(54) CLOSURE MECHANISM FOR SURGICAL TOOL

(71) Applicant: Ethicon LLC, Guaynabo, PR (US)

(72) Inventors: Mark D. Overmyer, Cincinnati, OH (US); Kris Eren Kallenberger, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 16/554,135

(22) Filed: Aug. 28, 2019

(65) Prior Publication Data
US 2021/0059773 A1  Mar. 4, 2021

(51) Int. Cl.
| | |
|---|---|
| *A61B 34/30* | (2016.01) |
| *A61B 17/072* | (2006.01) |
| *A61B 17/29* | (2006.01) |
| *A61B 34/37* | (2016.01) |

(52) U.S. Cl.
CPC ........ *A61B 34/30* (2016.02); *A61B 17/07207* (2013.01); *A61B 17/29* (2013.01); *A61B 34/37* (2016.02); *A61B 2017/07285* (2013.01); *A61B 2017/2943* (2013.01); *A61B 2034/302* (2016.02)

(58) Field of Classification Search
CPC ............. A61B 2017/07285; A61B 2017/2901; A61B 2017/2902; A61B 2017/2903; A61B 2017/2932; A61B 2017/2934; A61B 2017/2936; A61B 2017/2943; A61B 34/37; A61B 34/70; A61B 2034/302
See application file for complete search history.

(56) References Cited

U.S. PATENT DOCUMENTS

| | | | |
|---|---|---|---|
| 9,687,311 B2 | 6/2017 | Turner | |
| 9,869,339 B2 | 1/2018 | Zimmerman et al. | |
| 2007/0175956 A1* | 8/2007 | Swayze | A61B 34/76 227/178.1 |
| 2014/0000411 A1* | 1/2014 | Shelton, IV | A61B 34/37 74/650 |
| 2014/0276722 A1* | 9/2014 | Parihar | A61B 18/1482 606/33 |

(Continued)

OTHER PUBLICATIONS

ISR-WO from application PCT/IB2020/057730 dated Nov. 18, 2020 and that claims priority to the present U.S. application.

*Primary Examiner* — Martin T Ton
(74) *Attorney, Agent, or Firm* — Vorys, Sater, Seymour and Pease LLP

(57) ABSTRACT

A surgical tool includes a drive housing, a closure tube that extends from the drive housing, an end effector arranged at an end of the closure tube and having opposing jaws, and a closure yoke mounted to the closure tube and having a projection extending therefrom. A gearing assembly includes one or more spur gears attached to a corresponding one or more drive shafts such that rotation of the one or more drive shafts correspondingly rotates the one or more spur gears, and a closure cam gear positioned to intermesh with the one or more spur gears and defining a profile that receives the projection. Rotating the one or more spur gears causes the closure cam gear to rotate, which causes the projection to traverse the profile, and the projection traversing the profile urges the closure yoke and the closure tube to linearly displace and thereby actuate the jaws.

15 Claims, 15 Drawing Sheets

(56) References Cited

U.S. PATENT DOCUMENTS

| | | | |
|---|---|---|---|
| 2015/0201935 A1* | 7/2015 | Weisenburgh, II | ........................... A61B 17/3209 227/182.1 |
| 2018/0049813 A1* | 2/2018 | Yates | ..................... B25J 9/1689 |
| 2018/0168745 A1* | 6/2018 | Overmyer | .............. A61B 34/30 |
| 2019/0183592 A1* | 6/2019 | Shelton, IV | ........... A61B 34/70 |

* cited by examiner

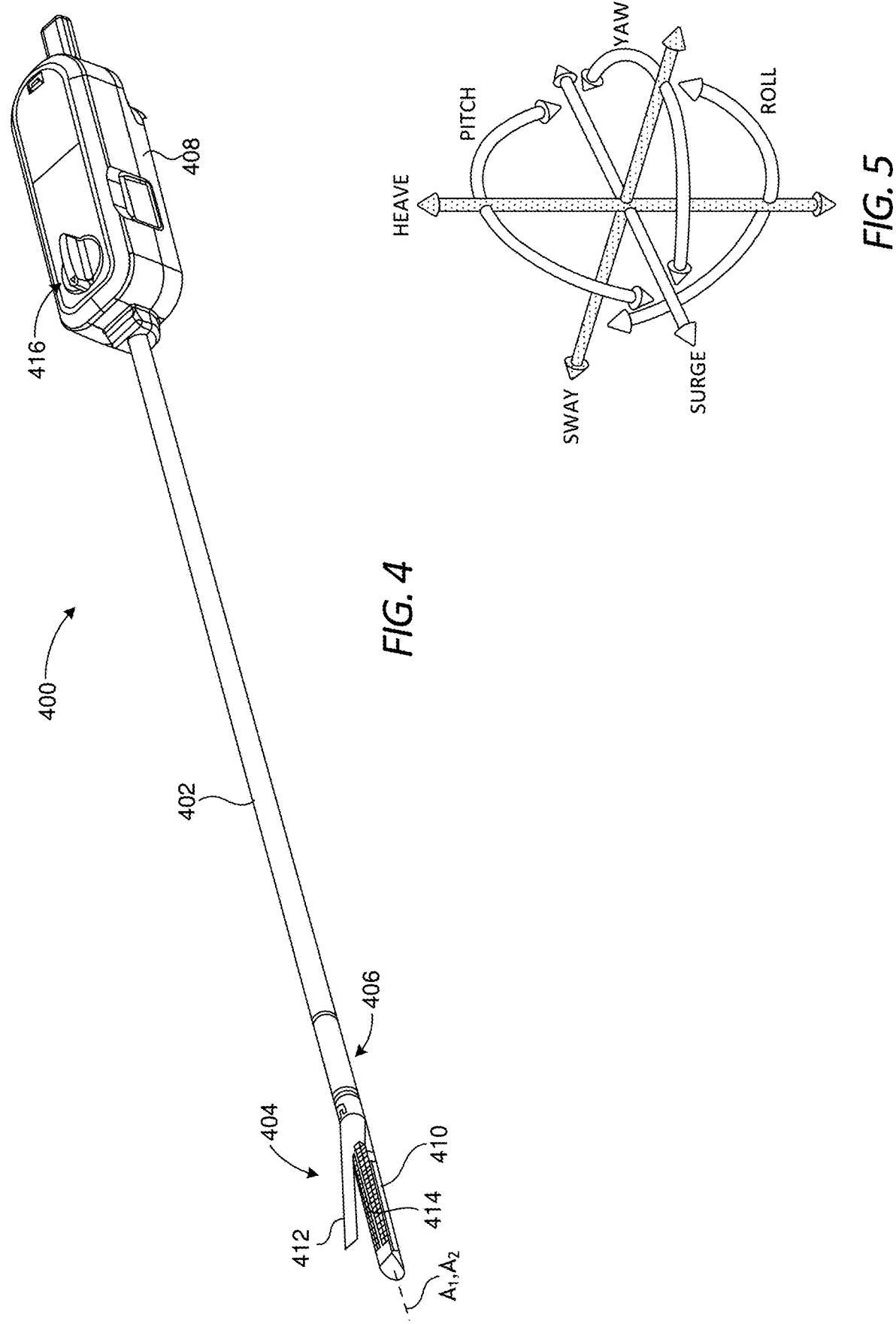

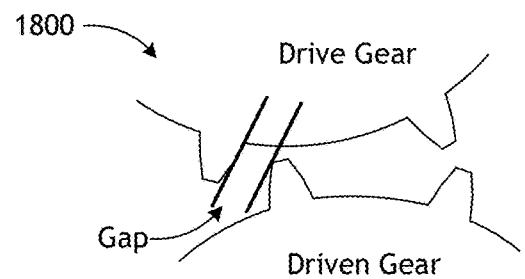
FIG. 17
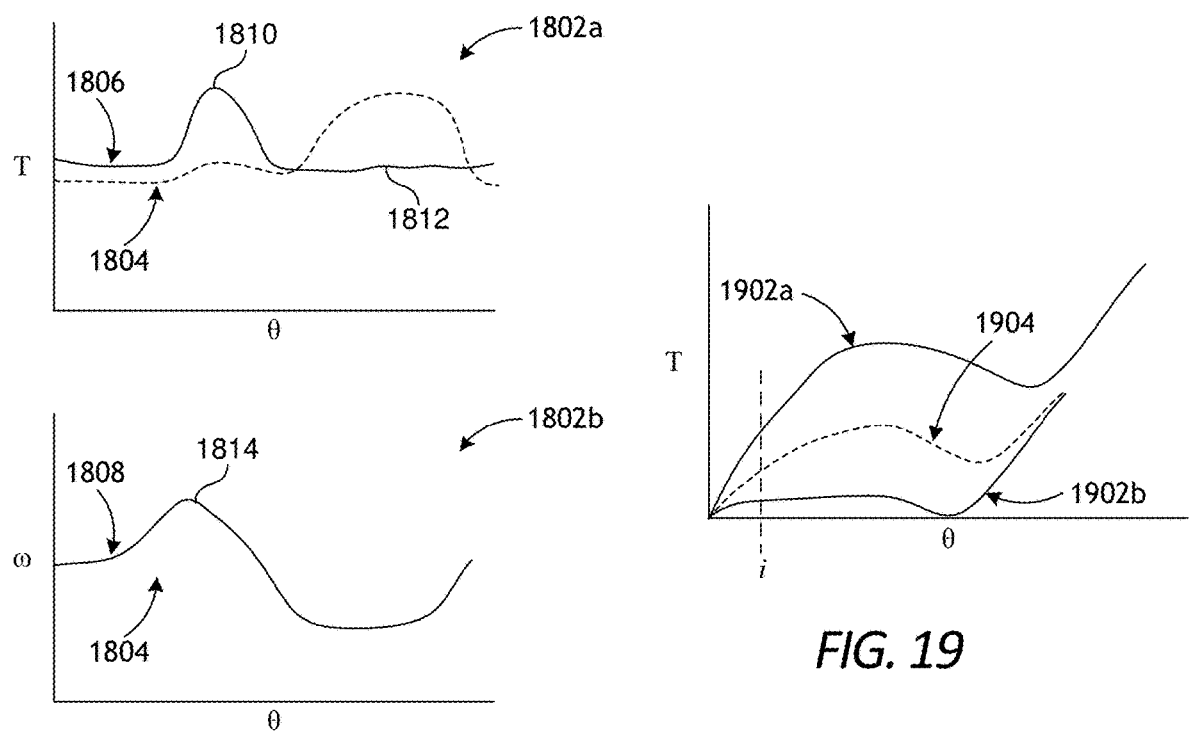
FIG. 18
FIG. 19

CLOSURE MECHANISM FOR SURGICAL TOOL

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, and needle holders, and are similar to those used in conventional (open) surgery except that the end effector of each tool is separated from its handle by an approximately 12-inch long, shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Surgical staplers are one type of end effector capable of cutting and simultaneously stapling (fastening) transected tissue. Alternately referred to as an "endocutter," the surgical stapler includes opposing jaws capable of opening and closing to grasp and release tissue. Once tissue is grasped or clamped between the opposing jaws, the end effector may be "fired" to advance a cutting element or knife distally to transect grasped tissue. As the cutting element advances, staples contained within the end effector are progressively deployed to seal opposing sides of the transected tissue.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 4 is an isometric side view of an example surgical tool that may incorporate some or all of the principles of the present disclosure.

FIG. 5 illustrates potential degrees of freedom in which the wrist of FIG. 4 may be able to articulate (pivot).

FIG. 17 is a schematic side view of an example gear interface that may help pulse the closing force on the jaws of FIG. 4.

FIG. 18 depicts a torque T versus angle $\Theta$ plot juxtaposed with an angular velocity $\omega$ versus angle $\Theta$ plot.

FIG. 19 a first torque-angle curve juxtaposed with a second torque-angle curve.

DETAILED DESCRIPTION

The present disclosure is related to robotic surgical tools and, more particularly, to closure systems and mechanisms for robotic surgical tools and monitoring the closure systems and mechanisms for efficient jaw closure and staple formation.

Figure 1:
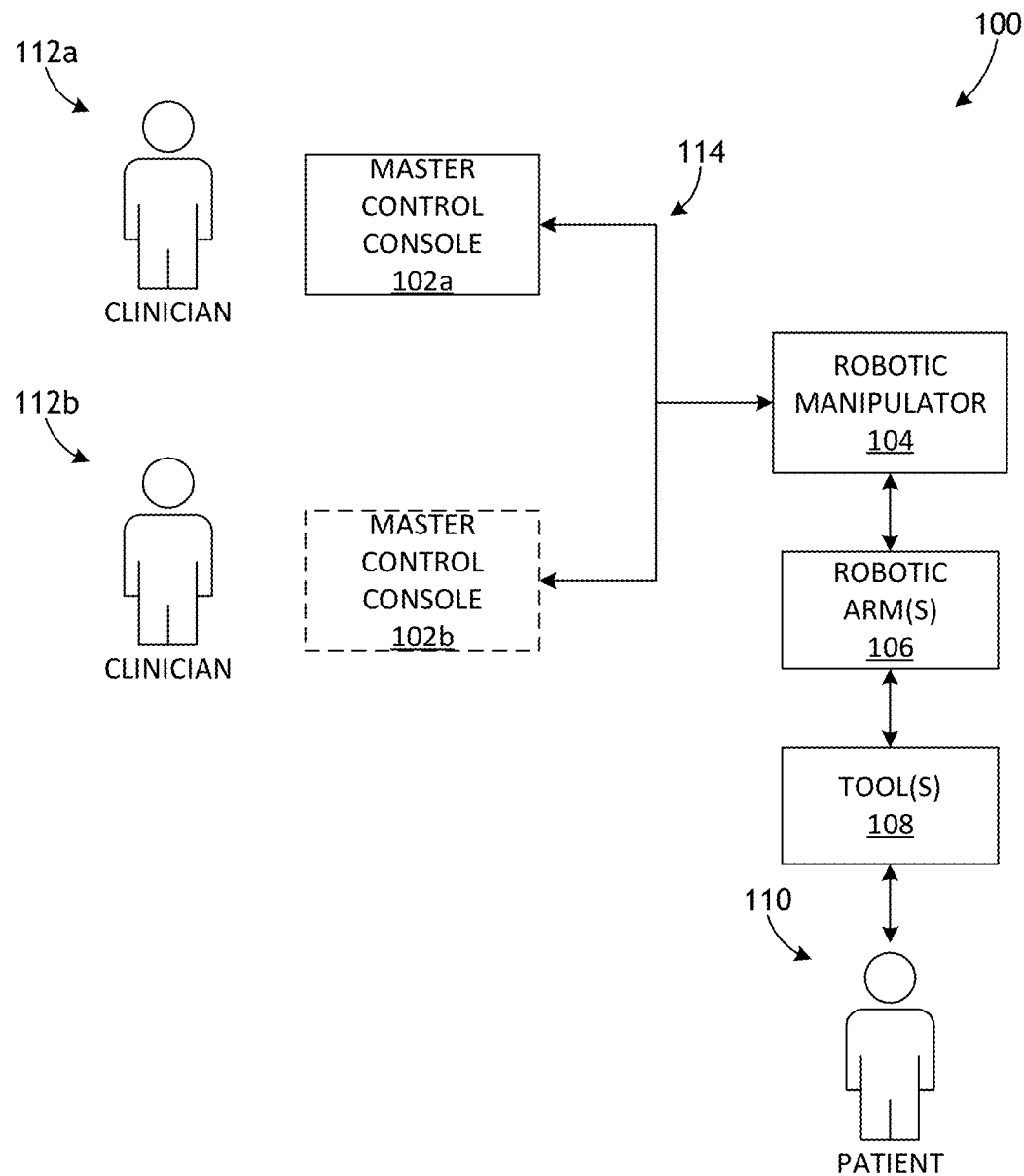
FIG. 1 is a block diagram of an example robotic surgical system that may incorporate some or all of the principles of the present disclosure.
Figure 3:
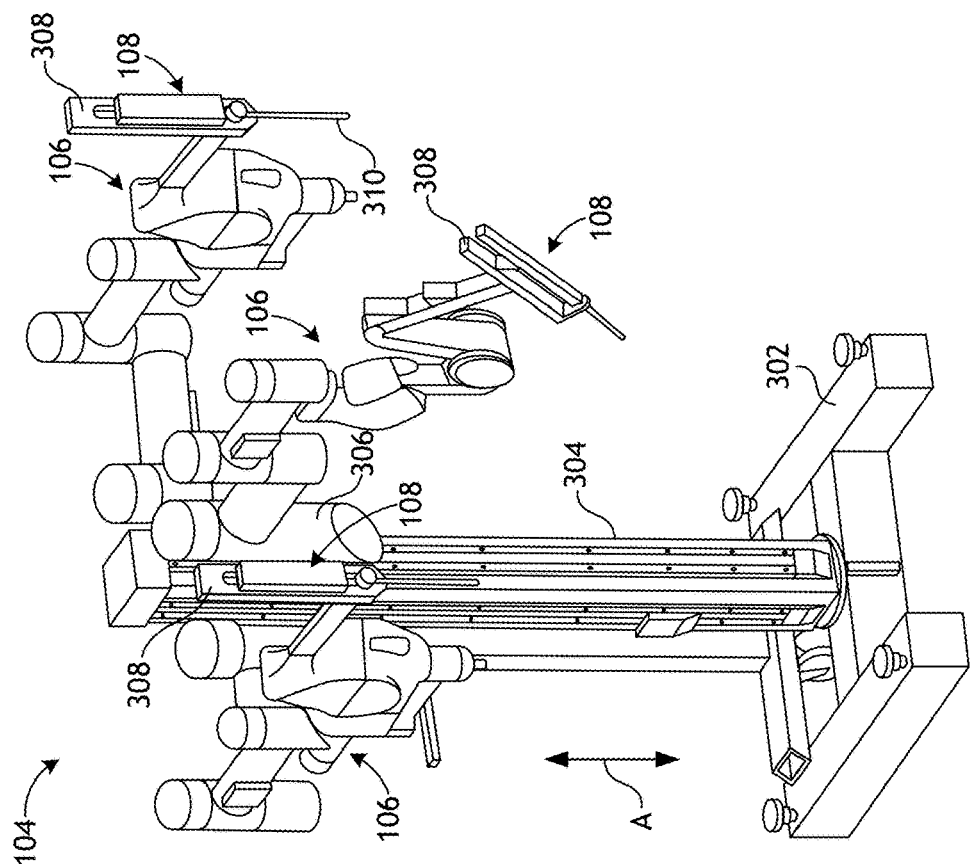
FIG. 3 depicts one example of the robotic manipulator of FIG. 1, according to one or more embodiments.
Figure 2:
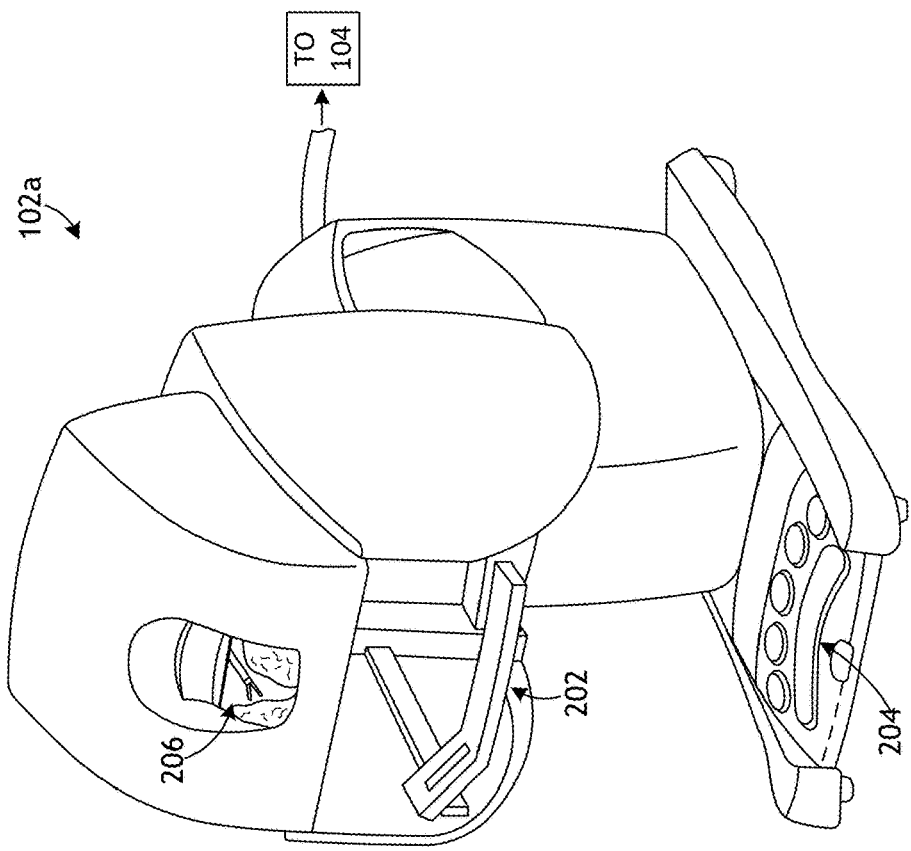
FIG. 2 is an example embodiment of one of the master control consoles of FIG. 1.

FIGS. 1-3 illustrate the structure and operation of an example robotic surgical system and associated components thereof. While applicable to robotic surgical systems, it is noted that the principles of the present disclosure may alternatively be applied to non-robotic surgical systems, without departing from the scope of the disclosure.

FIG. 1 is a block diagram of an example robotic surgical system 100 that may incorporate some or all of the principles of the present disclosure. As illustrated, the system 100 can include at least one master control console 102a and at least one robotic manipulator 104. The robotic manipulator 104 may be mechanically and/or electrically coupled to or otherwise include one or more robotic arms 106. In some embodiments, the robotic manipulator 104 may be mounted to a transport cart (alternately referred to as an "arm cart") that enables mobility of the robotic manipulator 104 and the associated robotic arms 106. Each robotic arm 106 may include and otherwise provide a tool driver where one or more surgical instruments or tools 108 may be mounted for performing various surgical tasks on a patient 110. Operation of the robotic arms 106, the corresponding tool drivers, and the associated tools 108 may be directed by a clinician 112a (e.g., a surgeon) from the master control console 102a.

In some embodiments, a second master control console 102b (shown in dashed lines) operated by a second clinician 112b may also help direct operation of the robotic arms 106 and the tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators having additional robotic arms may be utilized during surgery on a patient 110, and these additional robotic arms may be controlled by one or more of the master control consoles 102a,b.

The robotic manipulator 104 and the master control consoles 102a,b may communicate with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Accordingly, the clinicians 112a,b may be able to remotely control operation of the robotic arms 106 via the communications link 114, thus enabling the clinicians 112a,b to operate on the patient 110 remotely.

FIG. 2 is one example embodiment of the master control console 102a that may be used to control operation of the robotic manipulator 104 of FIG. 1. As illustrated, the master control console 102a can include a support 202 on which the clinician 112a,b (FIG. 1) can rest his/her forearms while gripping one or more user input devices (not shown). The user input devices can comprise, for example, physical controllers such as, but not limited to, hand-held actuator modules, a joystick, exoskeletal gloves, a master manipulator, etc., and may be movable in multiple degrees of freedom to control the position and operation of the surgical tool(s) 108 (FIG. 1). The master control console 102a may further include one or more foot pedals 204 engageable by the clinician 112a,b to change the configuration of the surgical system and/or generate additional control signals to control operation of the surgical tool(s) 108.

The user input devices and/or the foot pedals 204 may be manipulated while the clinician 112a,b (FIG. 1) views the procedure via a visual display 206. Images displayed on the visual display 206 may be obtained from an endoscopic camera or "endoscope." In some embodiments, the visual display 206 may include or otherwise incorporate a force feedback meter or "force indicator" that provides the clinician 112a,b with a visual indication of the magnitude of force being assumed by the surgical tool (i.e., a cutting instrument or dynamic clamping member) and in which direction. As will be appreciated, other sensor arrangements may be employed to provide the master control console 102a with an indication of other surgical tool metrics, such as whether a staple cartridge has been loaded into an end effector or whether an anvil has been moved to a closed position prior to firing, for example.

FIG. 3 depicts one example of the robotic manipulator 104 that may be used to operate a plurality of surgical tools 108, according to one or more embodiments. As illustrated, the robotic manipulator 104 may include a base 302 that supports a vertically extending column 304. A plurality of robotic arms 106 (three shown) may be operatively coupled to the column 304 at a carriage 306 that can be selectively adjusted to vary the height of the robotic arms 106 relative to the base 302, as indicated by the arrow A.

The robotic arms 106 may comprise manually articulable linkages, alternately referred to as "set-up joints." In the illustrated embodiment, a surgical tool 108 is mounted to corresponding tool drivers 308 provided on each robotic arm 106. Each tool driver 308 may include one or more drivers or motors used to interact with a corresponding one or more drive inputs of the surgical tools 108, and actuation of the drive inputs causes the associated surgical tool 108 to operate.

One of the surgical tools 108 may comprise an image capture device 310, such as an endoscope, which may include, for example, a laparoscope, an arthroscope, a hysteroscope, or may alternatively include some other imaging modality, such as ultrasound, infrared, fluoroscopy, magnetic resonance imaging, or the like. The image capture device 310 has a viewing end located at the distal end of an elongate shaft, which permits the viewing end to be inserted through an entry port into an internal surgical site of a patient's body. The image capture device 310 may be communicably coupled to the visual display 206 (FIG. 2) and capable of transmitting images in real-time to be displayed on the visual display 206.

The remaining surgical tools may be communicably coupled to the user input devices held by the clinician 112a,b (FIG. 1) at the master control console 102a (FIG. 2). Movement of the robotic arms 106 and associated surgical tools 108 may be controlled by the clinician 112a,b manipulating the user input devices. As described in more detail below, the surgical tools 108 may include or otherwise incorporate an end effector mounted on a corresponding articulable wrist pivotally mounted on a distal end of an associated elongate shaft. The elongate shaft permits the end effector to be inserted through entry ports into the internal surgical site of a patient's body, and the user input devices also control movement (actuation) of the end effector.

In use, the robotic manipulator 104 is positioned close to a patient requiring surgery and is then normally caused to remain stationary until a surgical procedure to be performed has been completed. The robotic manipulator 104 typically has wheels or casters to render it mobile. The lateral and vertical positioning of the robotic arms 106 may be set by the clinician 112a,b (FIG. 1) to facilitate passing the elongate shafts of the surgical tools 108 and the image capture device 310 through the entry ports to desired positions relative to the surgical site. When the surgical tools 108 and image capture device 310 are so positioned, the robotic arms 106 and carriage 306 can be locked in position.

FIG. 4 is an isometric side view of an example surgical tool 400 that may incorporate some or all of the principles of the present disclosure. The surgical tool 400 may be the same as or similar to at least one of the surgical tools 108 of FIGS. 1 and 3 and, therefore, may be used in conjunction with a robotic surgical system, such as the robotic surgical system 100 of FIG. 1. As illustrated, the surgical tool 400 includes an elongated shaft 402, an end effector 404, an articulable wrist 406 (alternately referred to as a "wrist joint") that couples the end effector 404 to the distal end of the shaft 402, and a drive housing 408 coupled to the proximal end of the shaft 402. In applications where the surgical tool 400 is used in conjunction with a robotic surgical system, the drive housing 408 can include coupling features that releasably couple the surgical tool 400 to the robotic surgical system. The principles of the present disclosure, however, are equally applicable to surgical tools that are non-robotic and otherwise capable of manual manipulation.

The terms "proximal" and "distal" are defined herein relative to a robotic surgical system having an interface configured to mechanically and electrically couple the surgical tool 400 (e.g., the drive housing 408) to a robotic manipulator. The term "proximal" refers to the position of an element closer to the robotic manipulator and the term "distal" refers to the position of an element closer to the end effector 404 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 400 can have any of a variety of configurations capable of performing one or more surgical functions. In the illustrated embodiment, the end effector 404 comprises a surgical stapler, alternately referred to as an "endocutter," configured to cut and staple (fasten) tissue. As illustrated, the end effector 404 includes opposing jaws 410, 412 configured to move (articulate) between open and closed positions. The opposing jaws 410, 412, however, may alternately form part of other types of end effectors that include jaws such as, but not limited to, tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. One or both of the jaws 410, 412 may be configured to pivot to actuate the end effector 404 between the open and closed positions. In the illustrated example, the second jaw 412 is rotatable (pivotable) relative to the first jaw 410 to move between an open, unclamped position and a closed, clamped position. In other embodiments, however, the first jaw 410 may move (rotate) relative to the second jaw 412, without departing from the scope of the disclosure.

In the illustrated example, the first jaw 410 may be characterized or otherwise referred to as a "cartridge" jaw, and the second jaw 412 may be characterized or otherwise referred to as an "anvil" jaw. The first jaw 410 may include a frame that houses or supports a staple cartridge, and the second jaw 412 is pivotally supported relative to the first jaw 410 and defines a surface that operates as an anvil to deform staples ejected from the staple cartridge during operation.

The wrist 406 enables the end effector 404 to articulate (pivot) relative to the shaft 402 and thereby position the end effector 404 at desired orientations and locations relative to a surgical site. FIG. 5 illustrates the potential degrees of freedom in which the wrist 406 may be able to articulate (pivot). The wrist 406 can have any of a variety of configurations. In general, the wrist 406 comprises a joint configured to allow pivoting movement of the end effector 404 relative to the shaft 402. The degrees of freedom of the wrist 406 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 404) with respect to a given reference Cartesian frame. As depicted in FIG. 5, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 406 (e.g., X-axis), yaw movement about a second axis of the wrist 406 (e.g., Y-axis), and combinations thereof to allow for 360° rotational movement of the end effector 404 about the wrist 406. In other applications, the pivoting motion can be limited to movement in a single plane, e.g., only pitch movement about the first axis of the wrist 406 or only yaw movement about the second axis of the wrist 406, such that the end effector 404 moves only in a single plane.

Referring again to FIG. 4, the surgical tool 400 may incorporate or include an actuation system designed to facilitate articulation of the wrist 406 and actuation (operation) of the end effector 404 (e.g., clamping, firing, rotation, articulation, energy delivery, etc.). The actuation system may include a plurality of drive members or the like (obscured in FIG. 4) that extend from the drive housing 408 to the wrist 406, and selective actuation of these drive members causes the end effector 404 to articulate (pivot) relative to the shaft 402 at the wrist 406. The end effector 404 is depicted in FIG. 4 in the unarticulated position where a longitudinal axis $A_2$ of the end effector 404 is substantially aligned with the longitudinal axis $A_1$ of the shaft 402, such that the end effector 404 is at a substantially zero angle relative to the shaft 402. In the articulated position, the longitudinal axes $A_1$, $A_2$ would be angularly offset from each other such that the end effector 404 is at a non-zero angle relative to the shaft 402.

Other drive members may extend to the end effector 404, and selective actuation of those drive members may cause the end effector 404 to actuate (operate). Actuating the end effector 404 may include closing and/or opening the second jaw 412 relative to the first jaw 410 (or vice versa), thereby enabling the end effector 404 to grasp (clamp) onto tissue. Once tissue is grasped or clamped between the opposing jaws 410, 412, actuating the end effector 404 may further include "firing" the end effector 404, which may refer to causing a cutting element or knife (not visible) to advance distally within a slot 414 defined in the second jaw 410. As it moves distally, the cutting element may transect any tissue grasped between the opposing jaws 410, 412. Moreover, as the cutting element advances distally, a plurality of staples contained within the staple cartridge (e.g., housed within the first jaw 410) may be urged (cammed) into deforming contact with corresponding anvil surfaces (e.g., pockets) provided on the second jaw 412. The deployed staples may form multiple rows of staples that seal opposing sides of the transected tissue.

In some applications, the surgical tool 400 may also be configured to apply energy to tissue, such as radio frequency (RF) energy. In such cases, actuating the end effector 404 may further include applying energy to tissue grasped or clamped between two opposing jaws to cauterize or seal the captured tissue, following which the tissue may be transected.

The surgical tool 400 may further include a manual jaw control system that enables a user to manually open and close the jaws 410, 412. In the illustrated embodiment, the manual jaw control system may include a control tool 416 accessible to a user on the exterior of the drive housing 408. The control tool 416 may be operatively coupled to various gears and/or drive members located within the drive housing 408 to allow a clinician to manually open and close the jaws 410, 412. By rotating the control tool 416 in either angular direction, a clinician may be able to fully clamp and fully unclamp the jaws 410, 412. The control tool 416 may be particularly useful to a clinician when the surgical tool 400 is detached from a surgical robot, since having the capability to open and close the jaws 410, 412 may eliminate the need to place inadvertent stress on internal drive members or components. In the event that a clinician desires to manually open the jaws 410, 412 when the surgical tool 400 is still attached to a surgical robot, the clinician can rotate the control tool 416 in an attempt to open the end effector 404.

Figure 6:
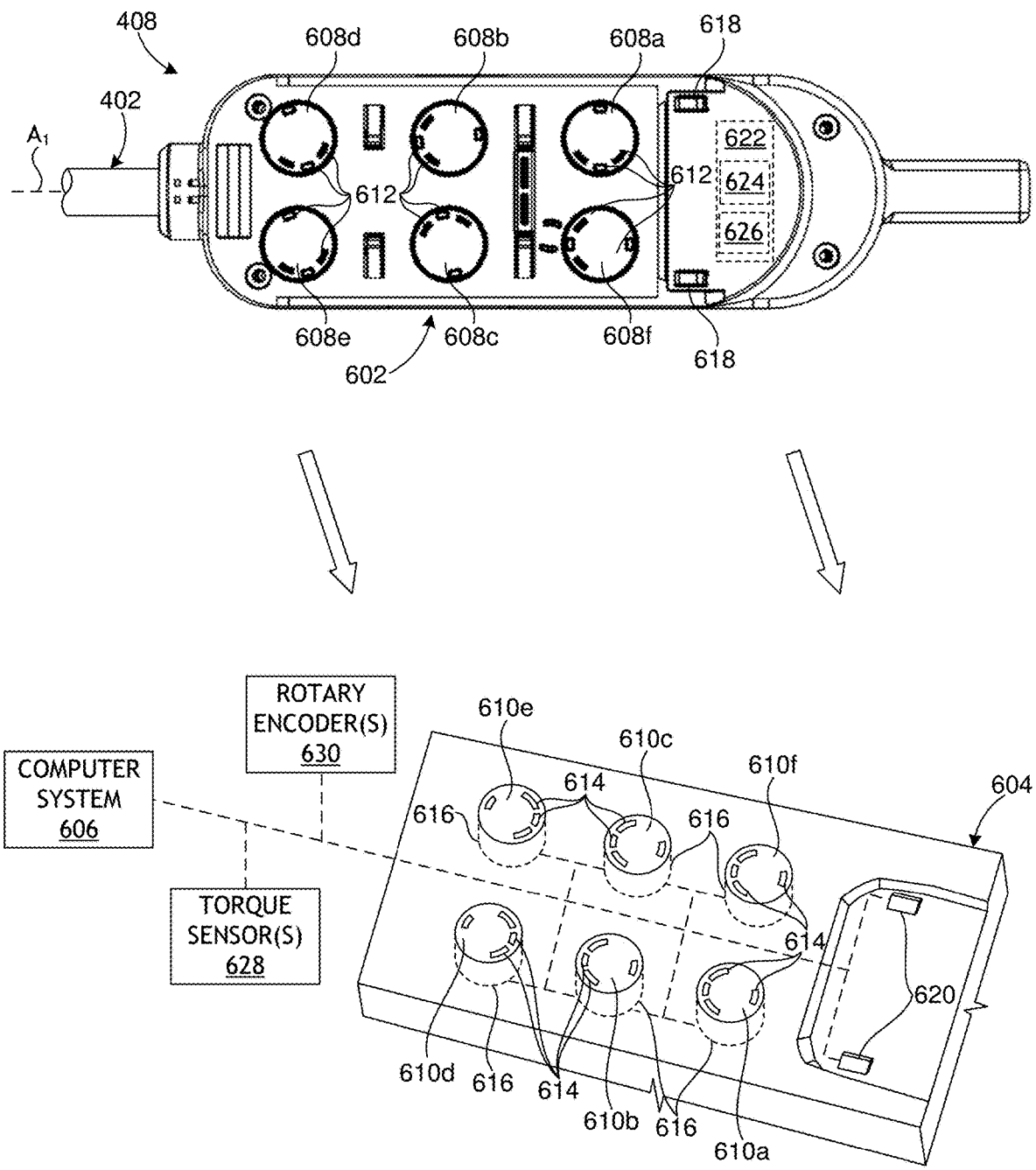
FIG. 6 is a bottom view of the drive housing of FIG. 4, according to one or more embodiments.

FIG. 6 is a bottom view of the drive housing 408, according to one or more embodiments. As illustrated, the drive housing 408 may include a tool mounting portion 602 used to operatively couple the drive housing 408 to a tool driver 604. The tool driver 604 may be the same as or similar to the tool drivers 308 of FIG. 3, and may thus be operable in conjunction with the robotic manipulator 104 of FIGS. 1 and 3. Mounting the drive housing 408 to the tool driver 604 places the drive housing 408 in communication with a computer system 606, which may communicate with or otherwise form part of the master controllers 102a,b (FIG. 1). The computer system 608 monitors and directs operation of the drive housing 408 via operation of the tool driver 604, thus enabling a user (e.g., the clinicians 112a,b of FIG. 1) to control operation of the drive housing 408 by working through the master controller 102a,b.

The tool mounting portion 602 includes and otherwise provides an interface that mechanically, magnetically, and/or electrically couples the drive housing 408 to the tool driver 604. In at least one embodiment, the tool mounting portion 602 couples the drive housing 408 to the tool driver 604 via a sterile barrier (not shown). As illustrated, the interface can include and support a plurality of inputs, shown as drive inputs 608a, 608b, 608c, 608d, 608e, and 608f. Each drive input 608a-f may comprise a rotatable disc configured to align (mate) with and couple to a corresponding driver 610a, 610b, 610c, 610d, 610e, and 610f of the tool driver 604. Each drive input 608a-f and corresponding driver 610a-f provide or define one or more matable surface features 612 and 614, respectively, configured to facilitate mating engagement between the opposing surface features 612, 614 such that movement (rotation) of a given driver 610a-f correspondingly moves (rotates) the associated drive input 608a-f.

Each driver 610a-f may include or otherwise comprise a motor 616 configured to actuate the corresponding driver 610a-f, and actuation of a given driver 610a-f correspondingly causes actuation of the mated drive input 608a-f, which facilitates operation of the mechanics of the drive housing 408. More specifically, actuation of a given motor 616 may cause rotational movement of the corresponding driver 610a-f, which, in turn, rotates the associated drive input 608a-f operatively coupled thereto. Each motor 616 may be in communication with the computer system 606 and, based on input signals provided by a user (e.g., a surgeon), the computer system 606 may selectively cause any of the motors 616 to actuate and thereby drive the corresponding driver 610a-f to operate the mechanical systems of the drive housing 408.

In some embodiments, actuation of the first drive input 608a via the first driver 610a may control rotation of the shaft 402 about its longitudinal axis $A_1$. Depending on the rotational direction of the first drive input 608a, the shaft 402 can be rotated clockwise or counter-clockwise, thus correspondingly rotating the end effector 404 (FIG. 4) in the same direction. Actuation of the second and third drive inputs 608b,c via the second and third drivers 610a,b, respectively, may control articulation of the end effector 404 at the wrist 406 (FIG. 4). Actuation of the fourth and fifth drive inputs 608d,e via the fourth and fifth drivers 610d,e, respectively, may cause an outer portion of the shaft 402 (referred to herein as a "closure tube") to advance and retract, which closes and opens the jaws 410, 412 (FIG. 4). Lastly, actuation of the sixth drive input 608f via the sixth driver 610f may cause the end effector 404 to fire, which may entail distal deployment of a cutting element to transect tissue grasped by the jaws 410, 412 and simultaneous deployment of staples contained within the staple cartridge housed within the first jaw 410.

The tool mounting portion 602 may further include one or more electrical connectors 618 (two shown) configured to mate with corresponding electrical connections 620 (two shown) provided by the tool driver 604 to facilitate communication between the drive housing 408 and the tool driver 604. Alternately, or in addition thereto, the drive housing 408 can wirelessly communicate with the tool driver 604, such as through a near field communication connection or protocol. The drive housing 408 may further house or otherwise include an internal computer 622 that may include a memory 624 and/or a microprocessor 626. The memory 624 may include one or more databases or libraries that store data relating to the drive housing 408 and, more particularly, to the surgical tool 400 (FIG. 4). In some embodiments, the memory 624 may include non-transitory, computer-readable media such as a read-only memory (ROM), which may be PROM, EPROM, EEPROM, or the like. Mating the drive housing 408 to the tool driver 604 places the internal computer 622 in communication with the computer system 606.

The computer system 606 may be programmed and otherwise configured to monitor operation of the surgical tool 400 (FIG. 4) using various sensors and/or electromechanical devices, collectively referred to herein as "monitoring devices." Each monitoring device may be designed to monitor one or more operational parameters of the surgical tool 400 and report measured operational parameters to the computer system 606 for processing. The computer system 606, for example, may be in communication with one or more torque sensors 628 and/or one or more rotary encoders 630, each of which may be characterized as a monitoring device designed to monitor operational parameters of the surgical tool 400. The torque sensors 628, for instance, may be configured to monitor torque, and the rotary encoders 630 may be configured to monitor motion (rotational or linear).

The torque sensors 628 and the rotary encoders 630 may be incorporated into the motors 616 of some or all of the drivers 610a-f, but could alternatively be operatively coupled to one or more of the drive inputs 608a-f. The torque sensors 628 may be configured to measure the real-time torque loading on the motors 616, which corresponds to the torque loading assumed by the drivers 610a-f and/or the drive inputs 608a-f. The rotary encoders 630 may measure the rotational motion or output of the motors 616, which corresponds to the rotational motion of the drivers 610a-f and/or the drive inputs 608a-f. Monitoring torque loading and rotational motion of the motors 616 may help determine if the surgical tool 400 is operating in accordance with the commands provided by the computer system 606.

Figure 7A:
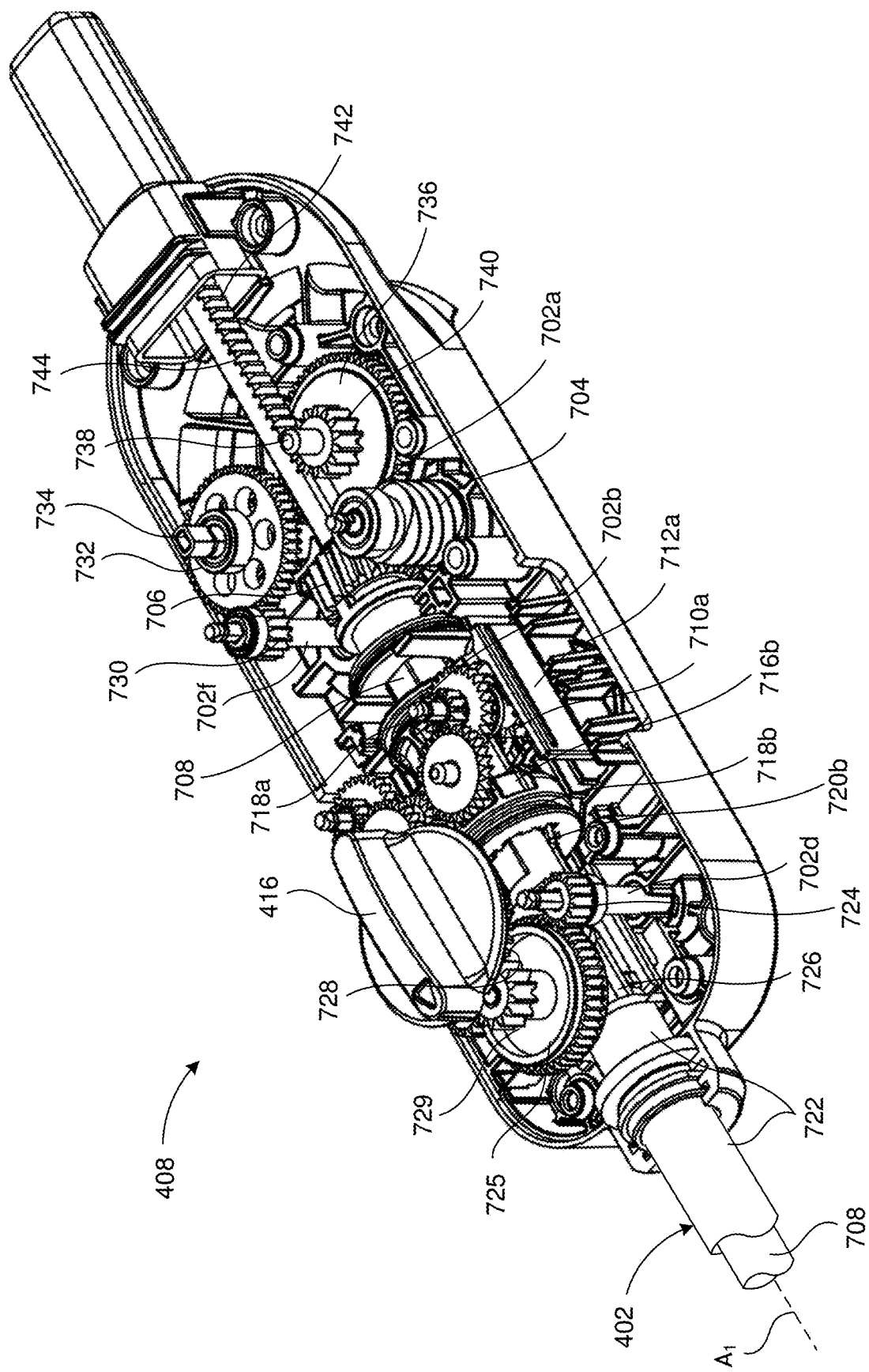
FIGS. 7A and 7B are exposed isometric views of the interior of the drive housing of FIG. 4, according to one or more embodiments.
Figure 7B:
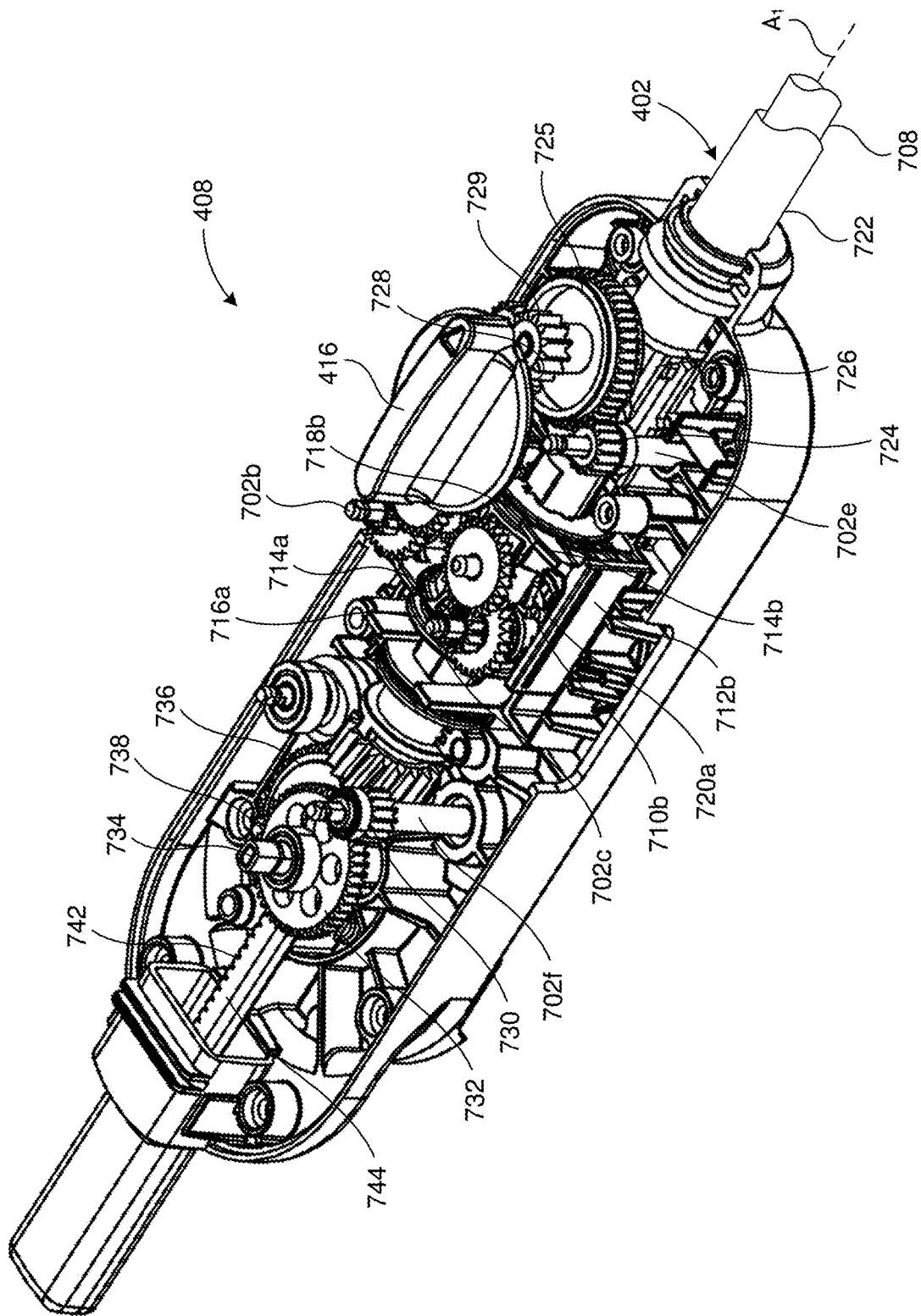

Referring to FIGS. 7A and 7B, illustrated are exposed isometric views of the interior of the drive housing 408, according to one or more embodiments. The upper portion of the drive housing 408 is omitted in FIGS. 7A-7B to allow viewing of the internal working components and parts. In addition, several component parts that would otherwise be included within the drive housing 408 are omitted in FIGS. 7A-7B to simplify the figures and enable discussion of the depicted component parts.

Referring first to FIG. 7A, a first drive shaft 702a is coupled to the first drive input 608a (FIG. 6) such that actuation and rotation of the first drive input 608a correspondingly rotates the first drive shaft 702a. A helical drive gear 704 is coupled to the first drive shaft 702a and rotates as the first drive shaft 702a rotates. The helical drive gear 704 intermeshes with a helical driven gear 706, which is operatively coupled to the shaft 402 and, more particularly, to an inner grounding shaft 708 that forms part of the shaft 402. The inner grounding shaft 708 extends concentrically within an outer portion of the shaft 402 referred to herein as the "closure tube." Accordingly, actuation of the first drive input 608a drives the first drive shaft 702a and correspondingly drives the inner grounding shaft 708 to rotate the shaft 402 about the longitudinal axis $A_1$.

A second drive shaft 702b may be coupled to the second drive input 608b (FIG. 6) such that actuation and rotation of the second drive input 608b correspondingly rotates the second drive shaft 702b. A pinion gear 710a (best seen in FIG. 7B) is attached to the second drive shaft 702b and is rotatable therewith. The pinion gear 710a intermeshes with a first driven rack 712a such that as the pinion gear 710a is rotated in a first rotational direction, the first driven rack 712a correspondingly translates in a first longitudinal direction. As the pinion gear 710a is rotated in a second rotational direction, the first driven rack 712a correspondingly translates in a second longitudinal direction opposite the first longitudinal direction.

The first driven rack 712a includes a first fork 714a (best seen in FIG. 7B) matable with a first articulation yoke 716a. More specifically, the first fork 714a is configured to be received within an annular slot 718a defined in the first articulation yoke 716a, which allows the first articulation yoke 716a to rotate about the longitudinal axis $A_1$ as the inner grounding shaft 708 rotates. Moreover, engagement between the first fork 714a and the annular slot 718a allows the first driven rack 712a to drive the first articulation yoke 716a along the longitudinal axis $A_1$ (distally or proximally) as acted upon by rotation of the second drive shaft 702b. As best seen in FIG. 7B, the first articulation yoke 716a may be coupled to a first drive member 720a, which extends distally to the wrist 406 (FIG. 4) along the shaft 402. Axial movement of the first articulation yoke 716a along the longitudinal axis $A_1$ correspondingly moves the first drive member 720a, which causes the wrist 406 and the end effector 404 (FIG. 4) to articulate.

Referring to FIG. 7B, a third drive shaft 702c is coupled to the third drive input 608c (FIG. 6) such that actuation and rotation of the third drive input 608c correspondingly rotates the third drive shaft 702c. A pinion gear 710b (best seen in FIG. 7A) is attached to the third drive shaft 702c and is rotatable therewith. The pinion gear 710b intermeshes with a second driven rack 712b such that rotating the pinion gear 710b in a first rotational direction correspondingly translates the second driven rack 712b in a first longitudinal direction. Rotating the pinion gear 710b in a second rotational direction correspondingly translates the second driven rack 712b in a second longitudinal direction opposite the first longitudinal direction.

The second driven rack 712b includes a second fork 714b matable with a second articulation yoke 716b. More particularly, the second fork 714b is configured to be received within an annular slot 718b (best seen in FIG. 7A) defined in the second articulation yoke 716b, which allows the second articulation yoke 716b to rotate about the longitudinal axis $A_1$ as the inner grounding shaft 708 rotates. Moreover, engagement between the second fork 714b and the annular slot 718b allows the second driven rack 712b to drive the second articulation yoke 716b along the longitudinal axis $A_1$ (distally or proximally) as acted upon by rotation of the third drive shaft 702c. As best seen in FIG. 7A, the second articulation yoke 716b may be coupled to a second drive member 720b, which extends distally to the wrist 406 (FIG. 4). Axial movement of the second articulation yoke 716b along the longitudinal axis $A_1$ correspondingly moves the second drive member 720b, which causes the wrist 406 and the end effector 404 (FIG. 4) to articulate.

Accordingly, axial movement of the first and second articulation yokes 716a,b along the longitudinal axis $A_1$ cooperatively actuates the drive members 720a,b and, thereby, articulates the end effector 404. The first and second articulation yokes 716a,b, for example, operate such that one of the articulation yokes 716a,b pulls one of the drive members 720a,b proximally while the other articulation yoke 716a,b pushes the other drive member 720a,b distally. However, the first and second articulation yokes 716a,b may alternatively be operated independently without the other being operated.

A fourth drive shaft 702d (FIG. 7A) and a fifth drive shaft 702e (FIG. 7B) may be coupled to the fourth and fifth drive inputs 604d,e (FIG. 6), respectively, such that actuation and rotation of the fourth and fifth drive inputs 604d,e correspondingly rotates the fourth and fifth drive shafts 702d,e. Rotation of the fourth and fifth drive shafts 702d,e may cause the jaws 410, 412 (FIG. 4) to move between open and closed positions. More specifically, the outer portion of the shaft 402 may comprise a closure tube 722 that is axially advanced or retracted by rotation of the fourth and fifth drive shafts 702d,e, and axially advancing and retracting the closure tube 722 correspondingly moves the jaws 410, 412 between open and closed positions. The following description of the gears and gearing assembly used to advance and retract the closure tube 722, and thereby move the jaws 410, 412 between open and closed positions, is provided in more detail with reference to FIGS. 8 and 9A-9B.

As illustrated, each drive shaft 702d,e has a spur gear 724 attached thereto, and both spur gears 724 are positioned to mesh with a closure cam gear 725 mounted to a closure yoke 726. The closure yoke 726 is rotatably mounted to the closure tube 722 but fixed axially thereto. This allows the closure tube 722 to rotate as the inner grounding shaft 708 rotates, but also allows the closure yoke 726 to advance or retract the closure tube 722. As described in more detail below, a projection (not shown) extends from or is otherwise coupled to the closure yoke 726, and the projection interacts with the closure cam gear 725 to facilitate axial movement of the closure yoke 726. Accordingly, rotating the spur gears 724 causes the closure cam gear 725 to rotate, which correspondingly causes the closure yoke 726 and the interconnected closure tube 722 to axially translate.

The closure cam gear 725 may also be operatively coupled (either directly or indirectly) to the control tool 416 arranged on the exterior of the drive housing 408 and forming part of the manual jaw control system. As best seen in FIG. 7A, a drive gear 728 may be positioned on the underside of the control tool 416 and may intermesh with a driven gear 729 operatively coupled to the closure cam gear 725. Consequently, a user can manually rotate the control tool 416, which will correspondingly rotate the drive gear 728 against the driven gear 729, and thereby cause the closure cam gear 725 to rotate and move the closure yoke 726 distally and proximally to close and open the jaws 410, 412 (FIG. 4).

A sixth drive shaft 702f is coupled to the sixth drive input 604f (FIG. 6) such that actuation and rotation of the sixth drive input 604f correspondingly rotates the sixth drive shaft 702f. Rotating the sixth drive shaft 702f may advance and retract a firing rod (not shown) that extends through the shaft 402 to the end effector 404 (FIG. 4). The distal end of the firing rod is operatively coupled to the cutting element (knife) such that axial movement of the firing rod correspondingly moves the cutting element distally or proximally to transect tissue grasped between the jaws 410, 412 (FIG. 4). In some embodiments, distal movement of the firing rod also deploys the staples, as described above.

A spur gear 730 is coupled to the sixth drive shaft 702f such that rotation of the sixth drive shaft 702f correspondingly rotates the spur gear 730. The spur gear 730 intermeshes with a second spur gear 732, which is attached to a first transfer drive shaft 734. A third spur gear (not visible) is coupled to the first transfer drive shaft 734 and intermeshes with a fourth spur gear 736, which is attached to a second transfer drive shaft 738. Finally, an output pinion gear 740 (FIG. 7A) is coupled to the second transfer drive shaft 738 and intermeshes with a rack gear 742 of a firing member 744 such that rotation of the output pinion gear 740 causes axial translation of the firing member 744. The firing member 744 may be coupled to the firing rod (not shown) discussed above. Accordingly, rotation of the sixth drive shaft 702f will drive the firing member 744 in axial translation, which correspondingly drives the firing rod in the same direction to advance and retract the cutting element at the end effector 404 (FIG. 4).

Figure 8:
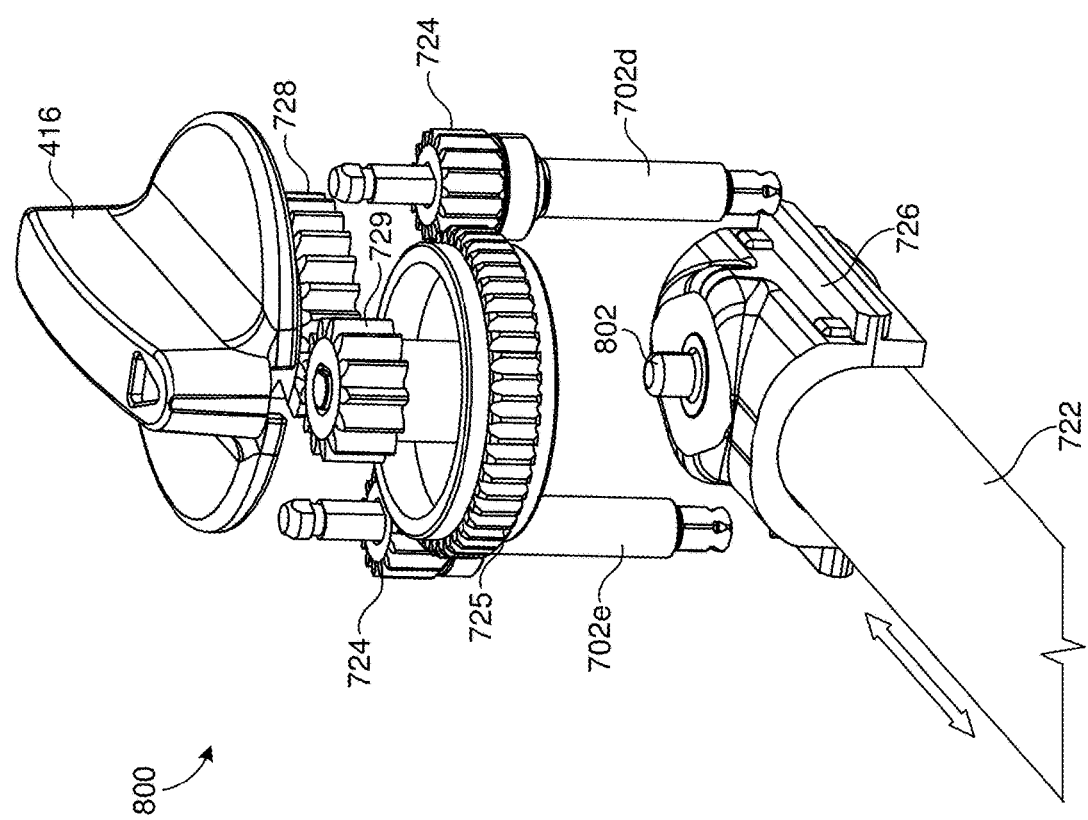
FIG. 8 is a partially exploded isometric view of an example gearing assembly 800 operable to move the closure tube of FIGS. 7A-7B and thereby open and close the jaws of FIG. 4.

FIG. 8 is a partially exploded isometric view of an example gearing assembly 800 operable to open and close the jaws 410, 412 (FIG. 4). The gearing assembly 800 is included in the drive housing 408 (FIGS. 7A-7B) and may be actuated to move (linearly displace) the closure yoke 726, which is rotatably mounted to the closure tube 722 but fixed axially thereto. As discussed above, moving the closure yoke 726 will correspondingly move the closure tube 722 in the same axial direction and thereby cause the jaws 410, 412 (FIG. 4) to close and open, depending on the movement of the closure tube 722.

Figure 9A:
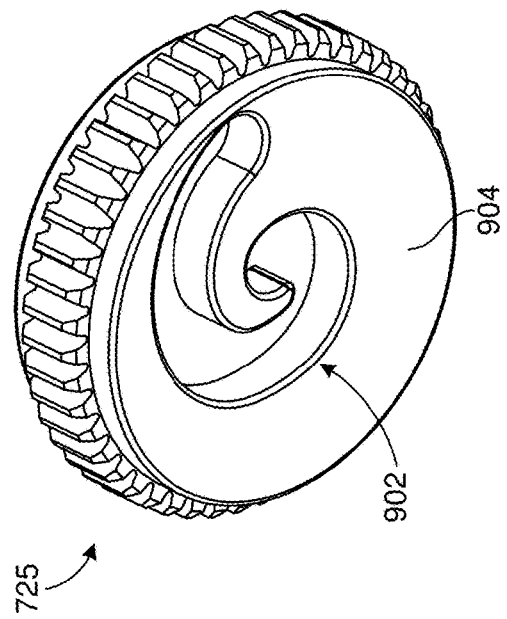
FIGS. 9A and 9B are isometric and bottom views, respectively, of the closure cam gear of the gearing assembly of FIG. 8.
Figure 9B:
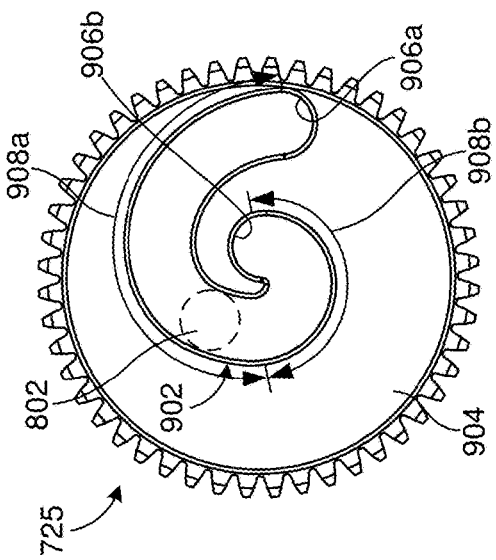

As illustrated, the gearing assembly 800 includes the closure cam gear 725, and FIGS. 9A and 9B are isometric and bottom views, respectively, of the closure cam gear 725. The gearing assembly 800 also includes the opposing spur gears 724 attached to the corresponding drive shafts 702d,e, and each spur gear 724 is positioned to intermesh with gear teeth defined on the outer periphery of the closure cam gear 725. Accordingly, rotating the drive shafts 702d,e causes the spur gears 724 to rotate the closure cam gear 725, which correspondingly moves the closure yoke 726 and the closure tube 722 distally and proximally to open and close the jaws 410, 412 (FIG. 4).

In the illustrated embodiment, the gearing assembly 800 may also include the drive gear 728 positioned on the underside of the control tool 416 and intermeshed with the driven gear 729 operatively coupled to the closure cam gear 725. A user can manually open and close the jaws 410, 412 by manually rotating the control tool 416, which correspondingly rotates the drive gear 728 against the driven gear 729, and thereby causes the closure cam gear 725 to rotate and move the closure yoke 726 and the closure tube 722 distally and proximally.

A projection 802 extends from or is otherwise coupled to the closure yoke 726. When the gearing assembly 800 is assembled in the drive housing 408 (FIGS. 4 and 7A-7B) the projection 802 interacts with the closure cam gear 725 to facilitate axial movement of the closure yoke 726 and the closure tube 722. As best seen in FIGS. 9A-9B, the projection 802 may be received within a profile 902 defined or otherwise formed in the bottom 904 of the closure cam gear 725. The profile 902 may operate as a camming profile or slot and, in some embodiments, may be generally in the shape of a spiral. As the closure cam gear 725 is rotated, the projection 802 slides within or otherwise follows the profile 902, and the curvature of the profile 902 urges the interconnected closure yoke 726 to translate longitudinally relative to the closure cam gear 725, which results in linear displacement of the interconnected closure tube 722. When the closure yoke 726 moves distally, the closure tube 722 correspondingly moves in the distal direction and causes the jaws 410, 412 (FIG. 4) to close. In contrast, when the closure yoke 726 moves proximally, the closure tube 722 correspondingly moves in the proximal direction and causes the jaws 410, 412 to open.

Referring to FIG. 9B, the profile 902 provides a first end 906a and a second end 906b. The projection 802 (shown in dashed line) may be able to traverse all or a portion of the profile 902 between the first and second ends 906a,b as the closure cam gear 725 rotates. The profile 902 provides a mechanical advantage that converts the rotary input of the closure cam gear 725 into linear displacement of the closure yoke 726 and the closure tube 722. The profile 902 can be mathematically defined and, therefore, the achieved mechanical advantage may be optimized, tuned, or otherwise maximized for the particular application. In some embodiments, for example, the profile 902 may comprise a simple spiral or curve that extends between the first and second ends 906a,b at a constantly changing radius (e.g., a constant slope). In such embodiments, the profile 902 will provide a constant mechanical advantage to linearly displace the closure tube 722 as the projection 802 traverses the profile between the first and second ends 906a,b.

In other embodiments, however, the profile 902 may provide two or more arcuate regions that exhibit differing camming profiles, which correspondingly changes the mechanical advantage along the entire profile 902, and particularly at the transition between the arcuate regions. In the illustrated embodiment, for example, the profile 902 is defined by or otherwise provides a first arcuate region 908a and a second arcuate region 908b. The first arcuate region 908a extends from the first end 906a of the profile 902, and the second arcuate region 908b extends from the first arcuate region 908a to the second end 906b of the profile 902. The first arcuate region 908a may be characterized as the "closure" region in which the jaws 410, 412 (FIG. 4) are closing to grasp onto tissue. In contrast, the second arcuate region 908b may be characterized as the "clamping" region in which the jaws 410, 412 (FIG. 4) begin clamping onto grasped tissue. Accordingly, the first and second arcuate regions 908a,b comprise contiguous portions of the profile 902.

The cam path radius across the first and second arcuate regions may be constantly changing. In the first arcuate region 908a, the rate of decrease is constant (i.e., constantly changing radius) and therefore yielding a constant slope; xx degrees of input angle yields $s_1$*xx of translation, where 51 represents the slope of the first arcuate region 908a). In the second arcuate region 908b, the rate of decrease is also constant (i.e., constantly changing radius) and therefore yielding a constant slope, but different from the value in the first arcuate region 908a; xx degrees of input angle yields $s_2$*xx of translation, where $s_2$ represents the slope of the second arcuate region 908b. Consequently, as the projection 802 traverses the first arcuate region 908a, the linear displacement of the closure yoke 726 (FIG. 8) and the closure tube 722 (FIG. 8) will be faster and with less output force as compared to traversing the second arcuate region 908b, where the linear displacement of the closure yoke 726 and the closure tube 722 will be slower but with more output force.

The mathematical function or curvature of the profile 902 can be customized across the arcuate regions 908a,b to optimize operation of the end effector 404 (FIG. 4) and actuation of the jaws 410, 412 (FIG. 4). More specifically, as the projection 802 traverses the first arcuate region 908a, the first constant slope 51 of the profile 902 results in a faster but less forceful linear displacement of the closure yoke 726 (FIG. 8) and the closure tube 722 (FIG. 8). This may prove advantageous in moving the jaws 410, 412 toward the closed position quickly but with a smaller amount of output force, which may not be needed until tissue is grasped. In contrast, as the projection 802 traverses the second arcuate region 908a, the second constant slope $s_2$ of the profile 902 results in a slower but more forceful linear displacement of the closure yoke 726 and the closure tube 722. This may prove advantageous in moving the jaws 410, 412 slower towards the end of the closure sequence and gripping tissue more forcefully. Accordingly, the profile 902 may be optimized or customized based on corresponding position of the closure tube 722, which will directly impact the position, speed, and output closing force provided by the jaws 410, 412.

Figure 10A:
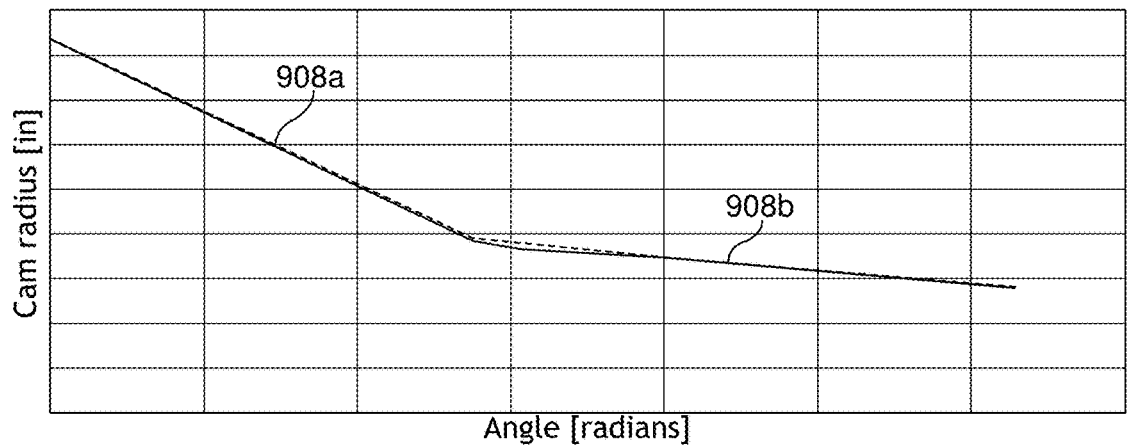
FIGS. 10A-10C are plots that graphically depict the change in mechanical advantage by transitioning between the first and second arcuate regions of the profile of FIGS. 9A-9B.
Figure 10B:
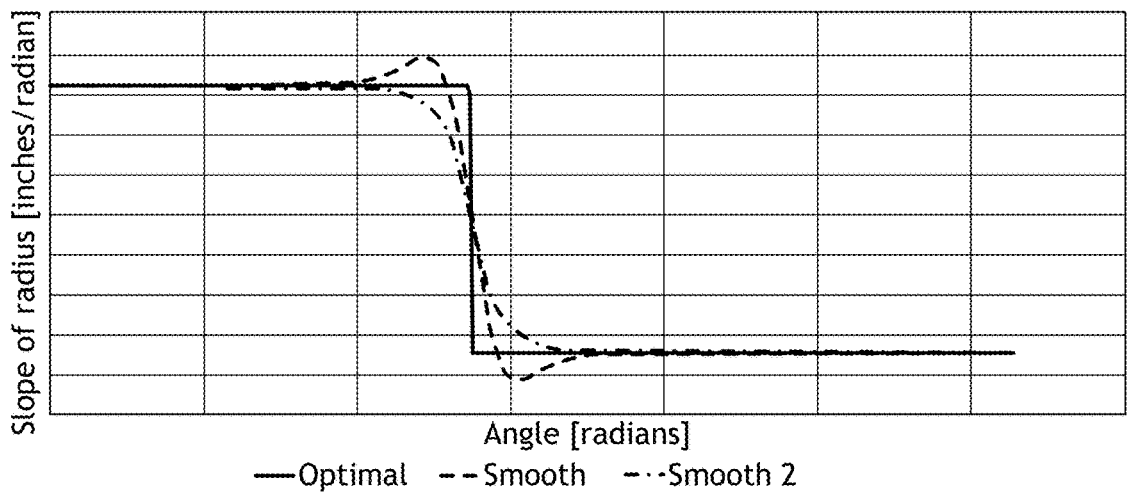
Figure 10C:
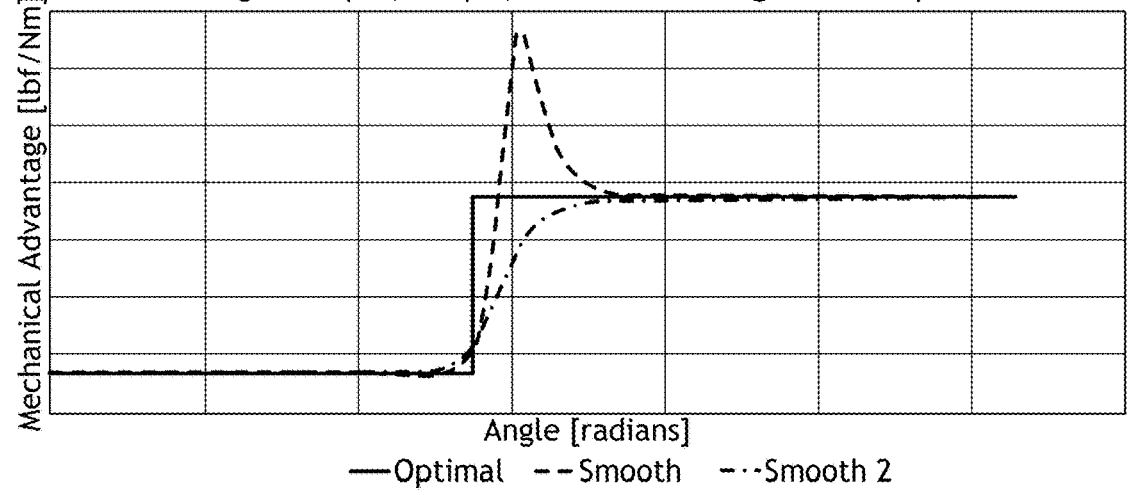

FIGS. 10A-10C are plots that graphically depict the change in mechanical advantage by transitioning between the first and second arcuate regions 908a,b of the profile 902 of FIGS. 9A-9B. As illustrated, the first arcuate region 908a results in a first mechanical advantage that is constant across the first arcuate region 908a, and the second arcuate region 908b results in a second mechanical advantage that is constant across the second arcuate region 908b but greater than the first mechanical advantage.

FIG. 10A shows a cartesian representation of the profile 902 of FIGS. 9A-9B. As indicated above, the profile 902 directly drives the location of the projection 802 (FIG. 8) on the closure yoke 726 (FIGS. 7A-7B and 8), and therefore the plot is also a representation of the position of the closure yoke as a function of the cam angle. The depicted line is representative of the constant slopes $s_1$, $s_2$ and the changes to the radius of the profile 902 (FIGS. 9A-9B). As illustrated, a large slope $s_1$ of the radius change (change in radius/cam angle) extends constant (straight) across the first arcuate region 908a, and transitions to a small slope $s_2$ of the radius change (change in radius/cam angle) that extends constant (straight) across the second arcuate region 908b.

In FIG. 10B, the depicted lines are representative of the slope of the profile 902 extending across the first and second arcuate regions 908a,b. As depicted, the slope of the profile 902 may be a step function with a smoothed transition. FIG. 10B is essentially the derivative of the position chart of FIG. 10A (e.g., dr/dt or the change is radius as a function of cam angle).

In FIG. 10C, the depicted line represents that for a given input torque (i.e., rotary input from the closure cam gear 725), the first and second arcuate regions 908a,b provide differing output forces (i.e., linear displacement of the closure tube 722). As depicted, the mechanical advantage across the second arcuate region 908b is greater than the mechanical advantage across the first arcuate region 908a, which equates to a more forceful output across the second arcuate region 908b as opposed to the across the first arcuate region 908a. Accordingly, FIG. 10C is a plot of the resultant theoretical output force delivered to the closure tube 722 (FIGS. 7A-7B and 8) given a constant input torque. It depicts two distinct regions of constant mechanical advantage and a transition region between them.

It is noted that while the profile 902 in FIGS. 9A-9B depicts two arcuate regions 908a,b, the profile 902 may be optimized or otherwise redesigned to include more than two regions, without departing from the scope of the disclosure. For instance, the profile 902 may include as many arcuate regions as necessary to alter the speed or the resulting output force at multiple locations along the curvature of the profile 902, all of which will correspond to the position and output force of the closure tube 722 in closing and opening the jaws 410, 412 (FIG. 4). Moreover, in some embodiments, the profile 902 may alternately include one or more straight regions, which would result in the closure tube 722 pausing briefly during opening and closing.

Controlling One Mechanism with Two Motors without Binding

Figure 11A:
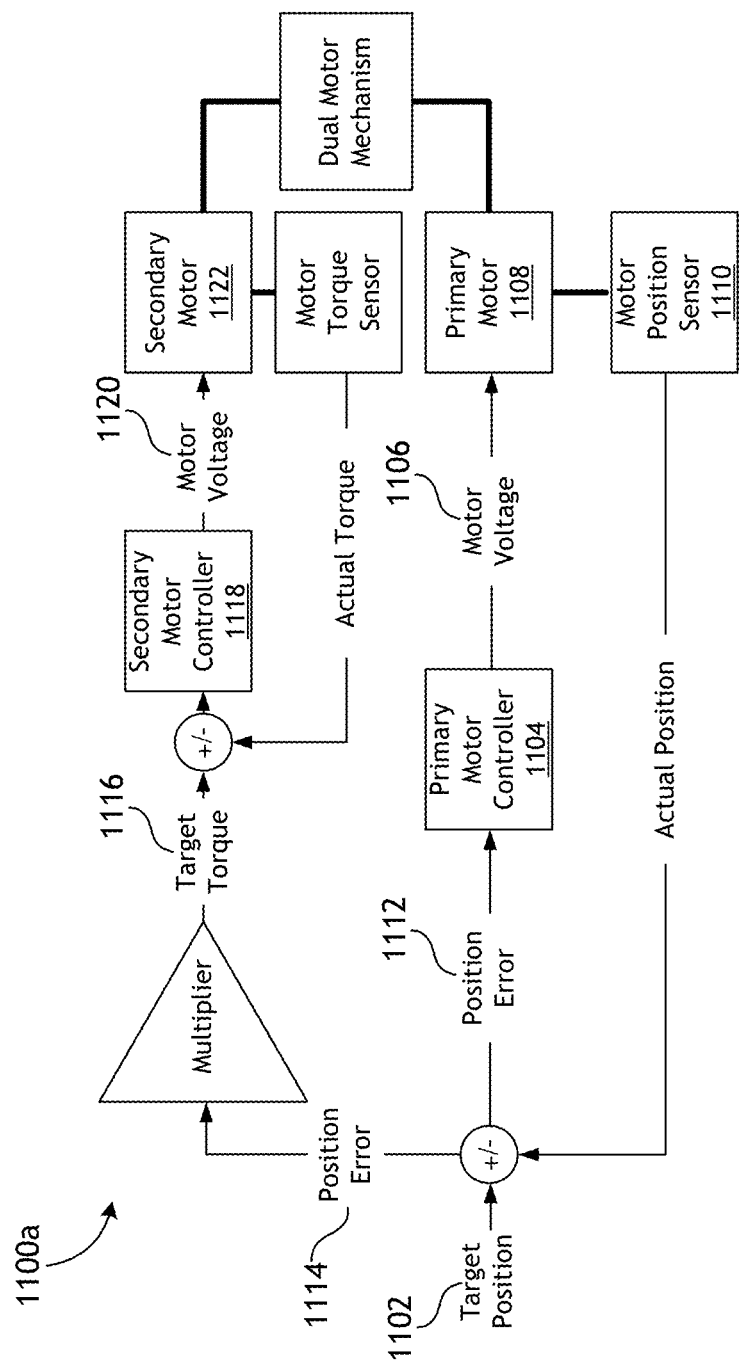
FIGS. 11A and 11B depict example control schematics for controlling one mechanism with two motors.
Figure 11B:
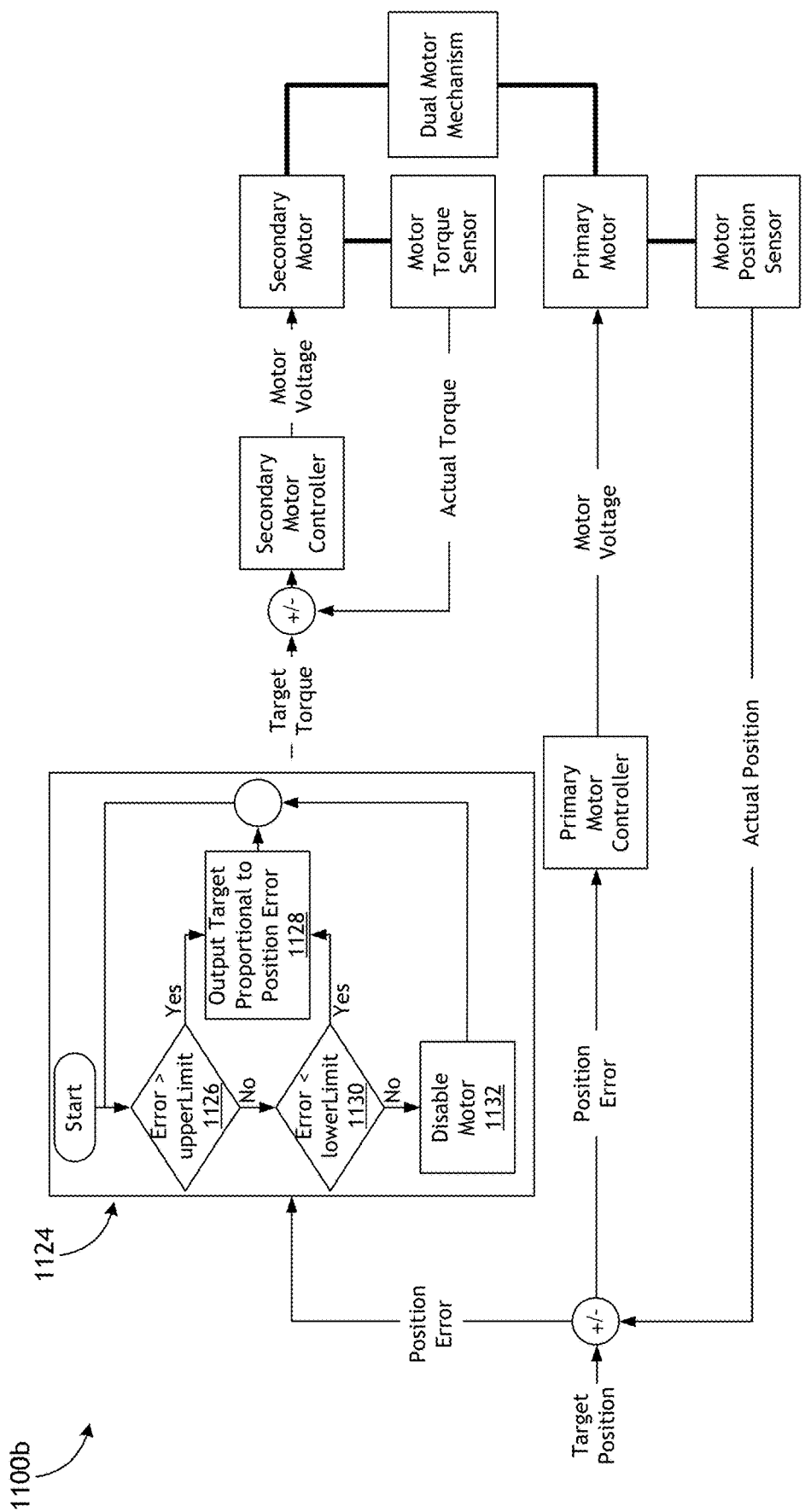

FIGS. 11A and 11B depict example control schematics 1100a and 1100b, respectively, for controlling one mechanism with two motors of a robotic surgical tool. Some robotic surgical tools utilize multiple rotary inputs from a tool driver to control one instrument degree of freedom. One example of this is the actuation and operation of the closure cam gear 725 (FIGS. 7A-7B, 8, 9A-9B), which causes the closure tube 722 (FIGS. 7A-7B, 8) to linearly displace and thereby open and close the jaws 410, 412 (FIG. 4). As described above, the closure cam gear 725 is rotated through actuation of the fourth and fifth drivers 610d,e (FIG. 6), which rotate the fourth and fifth drive inputs 608d,e (FIG. 6) and the interconnected fourth and fifth drive shafts 702d,e (FIGS. 7A-7B) to cause the pinions 724 (FIGS. 7A-7B, 8) attached to each drive shaft 702d,e to act on the closure cam gear 725. The motors 616 (FIG. 6) that operate the fourth and fifth drivers 610d,e need to be in sync or otherwise cooperatively operate or risk binding against the closure cam gear 725 during operation.

The first and second control schematics 1100a,b each control operation of a first or "primary" motor and a second or "secondary" motor. The primary and secondary motors may be, for example, the motors 616 (FIG. 6) that operate the fourth and fifth drivers 610d,e (FIG. 6) and thus cause operation (rotation) of the closure cam gear 725 (FIGS. 7A-7B, 8, 9A-9B) to move the closure tube 722 (FIGS. 7A-7B) and thereby open and close the jaws 410, 412 (FIG. 4). The first and second control schematics 1100a,b may comprise schematic algorithmic or software instructions that may be implemented (executed) by the computer system 606 of FIG. 6 to control simultaneous operation of the primary and secondary motors.

In FIG. 11A, the first control schematic 1100a includes providing a target position (or angle) to the primary motor, as at 1102, which produces some target clinical state (e.g., closure angle, articulation angle, etc.) for the surgical tool 400 (FIG. 4). A corresponding command is given to the primary motor via a primary motor controller, as at 1104, following which a corresponding voltage is applied, as at 1106, and the primary motor moves in response, as at 1108. The actual position of the corresponding drive input is then measured and compared against where it should be, as at 1110, and any position errors are accounted for by sending a new command to the primary motor, as at 1112. The position of the drive input can be measured using the rotary encoders 630 of FIG. 6, for example. This feedback loop keeps the primary motor moving and constantly readjusting to user specifications until the target position (angle) is met.

In accordance with the first control schematic 1100a, the position error of the primary motor may be sent to another controller, as at 1114, to allow the secondary motor to help the primary motor get the mechanism (e.g., the closure cam gear 725) to a desired orientation or position. The position error is sent to a multiplier, which outputs a target torque for the secondary motor, as at 1116. A corresponding command is given to the secondary motor via a secondary motor controller, as at 1118, following which a corresponding voltage is applied, as at 1120, and the secondary motor moves in response, as at 1122. The torque for the secondary motor is then measured, as at 1124, and may be measured using the torque sensors 628 of FIG. 6, for example. If the measured torque does not equal the target torque, the output of the secondary motor will be adjusted (i.e., increased or decreased) to minimize the error. Accordingly, the farther the primary motor is from its target position (angle), the harder the secondary motor will push to help supplement the primary motor. Operation of the secondary motor is reactive to the changes in the primary motor, and this secondary feedback loop helps keep the secondary motor moving and constantly readjusting to user specifications until the primary motor meets the target clinical state (e.g., target position, angle, etc.).

In FIG. 11B, the second control schematic 1100b is substantially similar to the first control schematic 1100a, but adds logic that if the position error provided from the primary motor is sufficiently close to zero, the secondary motor is disabled (e.g., allowed to freewheel by electrically disconnecting the motor from control circuitry) and thus does not risk binding against (impeding) operation of the primary motor. More specifically, the second control schematic 1100b may include a logic step 1124 that first determines if the position error of the primary motor is greater than a predetermined upper limit, as at 1126. If yes, then the secondary motor is operated based on an output target torque that is proportional to the position error, as at 1128, and operation of the secondary motor proceeds as described above with respect to the first control schematic 1100a.

If the position error of the primary motor is not greater than the predetermined upper limit, then it is determined if the position error of the primary motor is less than a predetermined lower limit, as at 1130. If the position error of the primary motor is less than the predetermined lower limit, then the secondary motor is operated based on an output target torque that is proportional to the position error, as at 1128, and operation of the secondary motor proceeds as described above with respect to the first control schematic 1100a. If no, then the secondary motor is disabled, as at 1132. In some embodiments, disabling the secondary motor may allow the secondary motor to free wheel as the primary motor operates.

Method of Closure Error Identification Using Thick Tissue Lockout

Figure 12A:
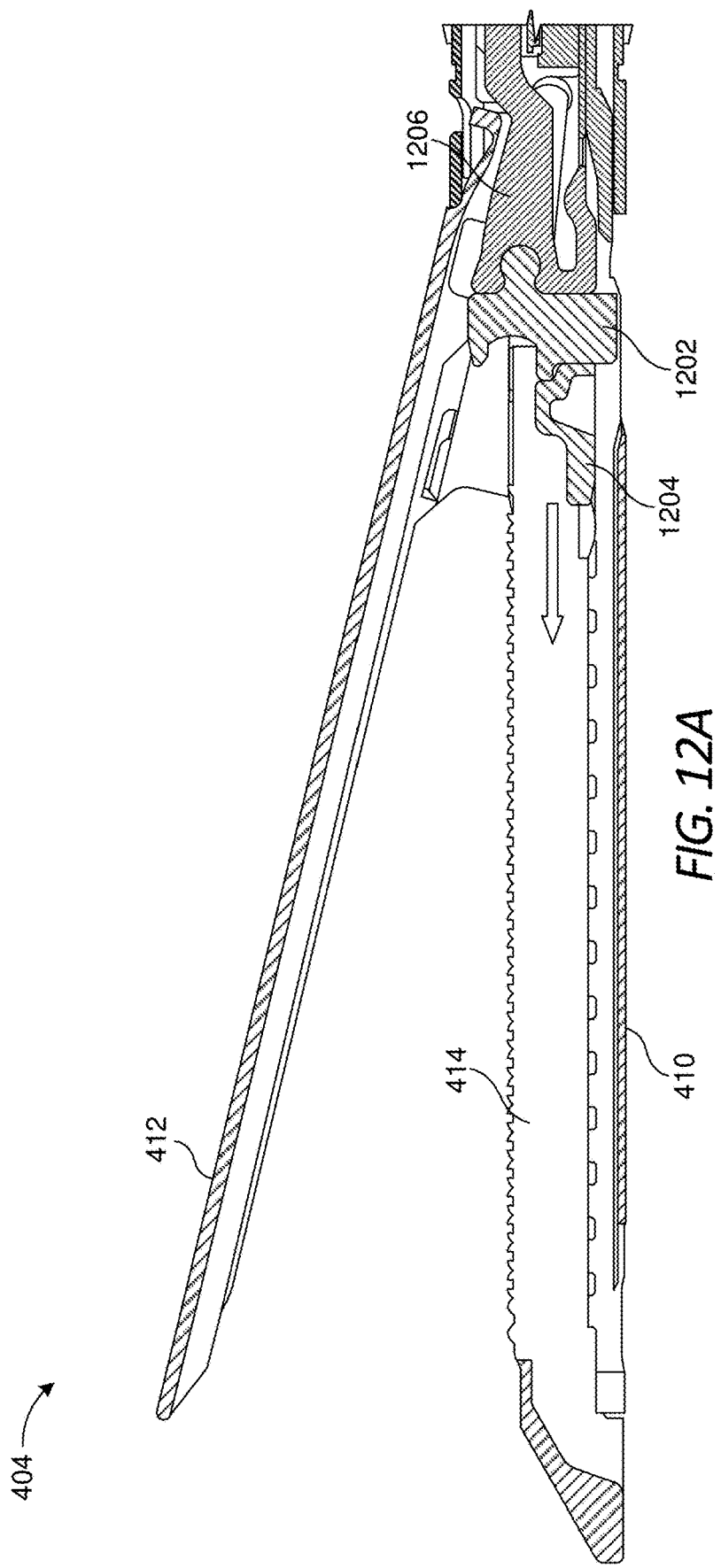
FIG. 12A is a cross-sectional side view of the end effector of FIG. 4.
Figure 12B:
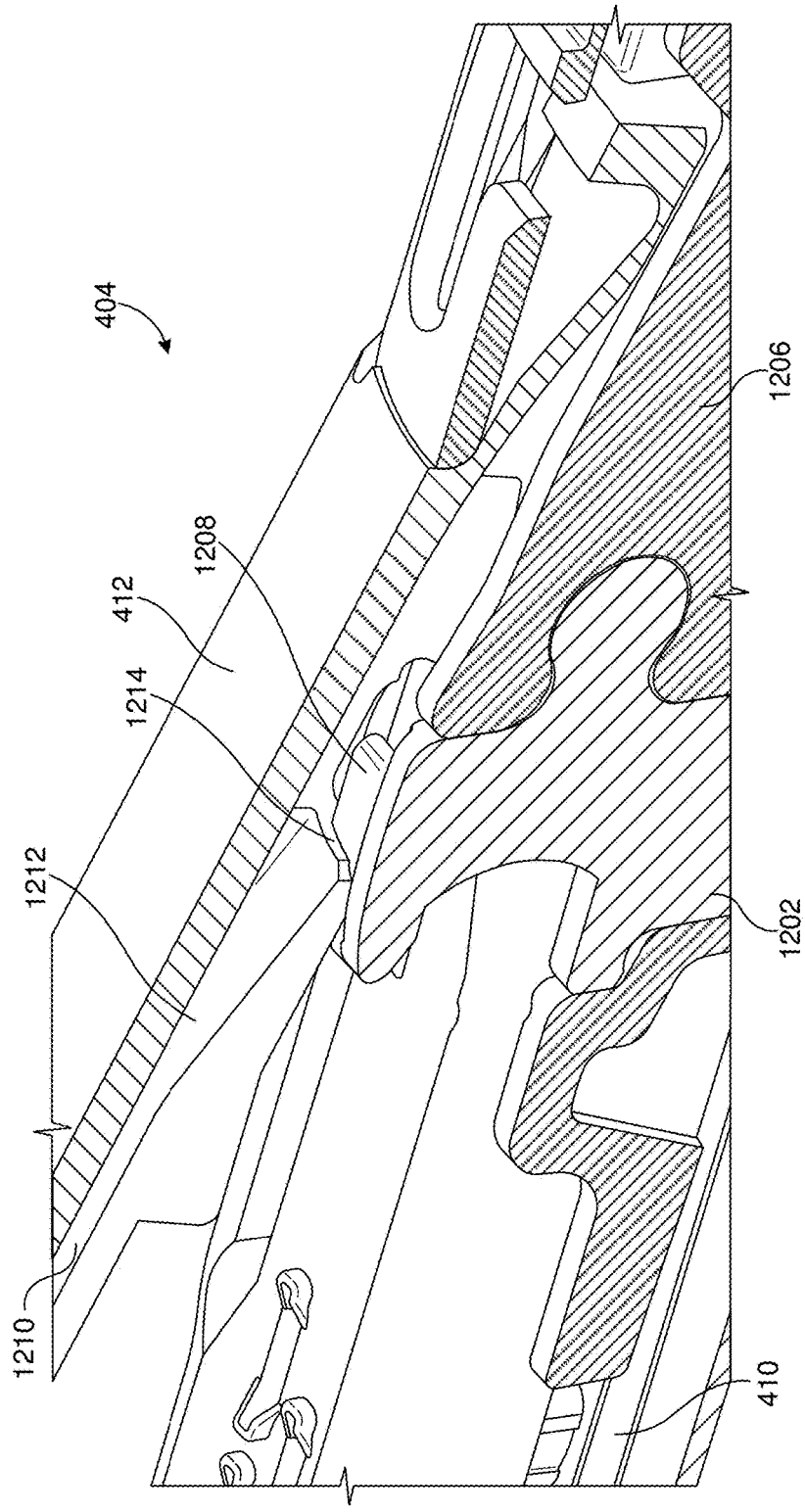
FIG. 12B is an enlarged, cross-sectional isometric view of a portion of the end effector of FIG. 12A.

FIG. 12A is an enlarged cross-sectional side view of the end effector 404 of FIG. 4, and FIG. 12B is an enlarged, cross-sectional isometric view of a portion of the end effector 404, according to one or more embodiments. Referring first to FIG. 12A, as mentioned above, the end effector 404 includes opposing jaws 410, 412 movable between open and closed positions, and the jaws 410, 412 are depicted in FIG. 12A in the open position. The end effector 404 may further include a cutting element or knife 1202 that can be linearly displaced within the slot 414 defined in the second jaw 410 to cut tissue grasped between the jaws 410, 412. As the knife 1202 advances distally within the slot, a sled or camming wedge 1204 simultaneously engages a plurality of staples (not shown) contained within the first jaw 410 (e.g., within a staple cartridge) and urges (cams) the staples into deforming contact with the opposing anvil surfaces (e.g., pockets) provided on the second jaw 412. Properly deployed staples help seal opposing sides of the transected tissue.

As illustrated, the cutting element 1202 is operatively coupled to a firing rod 1206 that extends proximally (i.e., to the right in FIG. 12A) and is operatively coupled to the firing member 744 of FIGS. 7A-7B at its proximal end. Actuation of the firing member 744, as generally described above, causes the firing rod 1206 to advance and retract and correspondingly advance and retract the knife 1202 so that it can transect tissue grasped between the jaws 410, 412. Distal movement of the firing rod 1206 also correspondingly moves the camming wedge 1204 to deploy the staples, as described above.

Referring now to FIG. 12B, with continued reference to FIG. 12A, a knife stop 1208 extends laterally from the knife 1202, and the upper jaw 412 provides or otherwise defines a channel 1210 sized to receive the knife stop 1208 as the knife 1202 moves distally. The channel 1210 also includes a ramped surface 1212, and the knife stop 1208 is required to traverse the ramped surface 1212 to fully enter the channel 1210.

A jaw stop 1214 may be provided at the proximal end of the channel 1210 and/or the ramped surface 1212. The jaw stop 1214 may be configured to stop distal movement of the knife 1202 when the jaws 410, 412 are open. More specifically, when the jaws 410, 412 are open, as shown in FIG. 12B, the jaw stop 1214 will be positioned such that the knife stop 1208 will engage the jaw stop 1214 and thereby stop distal movement of the knife 1202. In contrast, when the jaws 410, 412 are closed or substantially closed, the jaw stop 1214 will be moved downward and otherwise positioned such that the knife stop 1208 will be able to traverse the ramped surface 1212 and enter the channel 1210 when the knife 1202 is moved distally.

As described above with reference to FIGS. 7A-7B, the sixth drive input 604f (FIG. 6) may be actuated to advance and retract the firing rod 1206 and thereby advance and retract the knife 1206. At least one of the motors 616 of FIG. 6 controls actuation of the sixth drive input 604f, and operation of the motor 616 may be monitored with one or more corresponding torque sensors 628 (FIG. 6) and/or rotary encoders 630 (FIG. 6). If the firing rod 1206 is advanced distally when the jaws 410, 412 are open, the knife stop 1208 will run into (engage) the jaw stop 1214 and stop distal movement of the knife 1202, thus resulting in a torque spike measured by the torque sensor 628 that monitors operation of the motor 616 driving the sixth drive input 610f. Registering the torque spike will provide a positive indication that the knife stop 1208 has run into the jaw stop 1214 because the jaws 410, 412 are open. The computer system 606 (FIG. 6) may then prevent further distal movement of the knife 1202 as a protection measure.

When the jaws 410, 412 are closed, the firing rod 1206 may be advanced distally and the knife stop 1208 will traverse the ramped surface 1212 to enter the channel 1210. Traversing the ramped surface 1212 will register a torque spike as measured by the torque sensor 628 (FIG. 6), however, the torque spike recorded for traversing the ramped surface 1212 will be much less than the torque spike resulting from the knife stop 1208 engaging the jaw stop

1214 and stopping distal movement. The computer system 606 (FIG. 6) may have stored therein a known range of torque spikes that are anticipated when the knife stop 1208 traverses the ramped surface 1212 and enters the channel 1210 with the jaws 410, 412 closed. If the measured torque spike falls within this known range, then the computer system 606 can conclude that the knife stop 1208 is traversing the ramped surface 1212 and allows the firing sequence to continue. Accordingly, registering the smaller torque spike within the known range of torque spikes will provide a positive indication that the knife stop 1208 has successfully traversed the ramped surface 1212 and entered the channel 1210.

When the jaws 410, 412 are substantially closed but not fully closed, however, the knife stop 1208 may still be able to traverse the ramped surface 1212 and enter the channel 1210, but a larger torque spike may be measured. The jaws 410, 412 may not fully close for a variety of reasons, such as when the jaws 410, 412 grasp onto thick or large tissue. If the jaws 410, 412 are not fully closed, the staples may not be deployed accurately or appropriately when the end effector 404 is fired. Moreover, if the jaws 410, 412 are not fully closed, the angle of the ramped surface 1212 relative to the knife stop 1208 will be greater as compared to when the jaws 410, 412 are fully closed. Consequently, the torque spike measured by the torque sensor 628 (FIG. 6) will be greater than the known range of torque spikes anticipated when the knife stop 1208 traverses the ramped surface 1212 with the jaws 410, 412 fully closed. For example, the measured torque when the jaws 410, 412 are closed may be about 0.1 N·m, but could jump to about 0.3 N·m if the jaws are not fully closed. Accordingly, if a torque spike is measured between the known range of torque spikes and the torque spike registered when the knife stop 1208 engages the jaw stop 1214, that may be a positive indication that the jaws 410, 412 are substantially closed but not fully closed. According to embodiments of the present disclosure, the computer system 606 (FIG. 6) may be programmed to notify (alert) a user when the end effector 404 is being fired with the jaws 410, 412 substantially closed but not fully closed. This informs the user that there is a chance that the staples will not form appropriately if firing proceeds.

Figure 13:
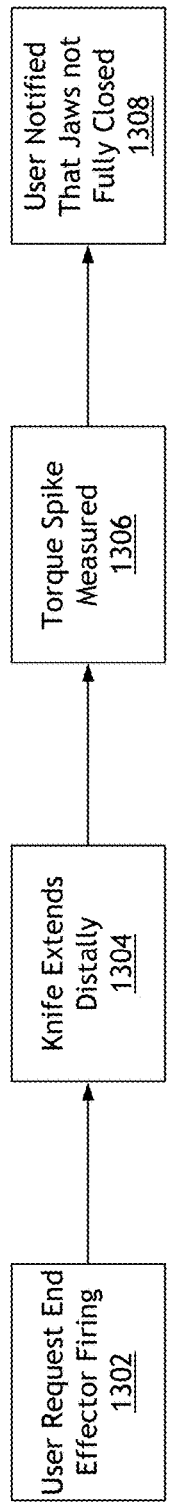
FIG. 13 is a schematic flowchart of an example method of monitoring torque spikes while firing the end effector of FIGS. 4 and 12A-12B.

FIG. 13 is a schematic flowchart of an example method 1300 of monitoring torque spikes while firing the end effector 404, according to one or more embodiments. The steps of the method 1300 may be implemented using the computer system 606 of FIG. 6 to help notify (alert) a user when the end effector 404 is being fired with the jaws 410, 412 not fully closed. As illustrated, the method 1300 may commence when a user requests that the end effector 404 be fired, as at 1302. More specifically, the user may be able to manipulate the user input devices in communication with the computer system 606 and send a command signal to fire the end effector 404. As indicated above, firing the end effector may cause the firing rod 1206 (FIGS. 12A-12B) to move and correspondingly advance the knife 1202 (FIGS. 12A-12B) distally, as at 1304, to transect any tissue grasped between the opposing jaws 410, 412. Firing the end effector 404 may also cause staples to be deployed to seal opposing sides of the transected tissue. As the firing rod 1206 and the knife 1202 advance distally, the torque on the motor (e.g., motors 616 of FIG. 6) causing the distal displacement is measured, and any torque spikes are measured, as at 1306. If a torque spike is measured that falls within a predetermined range of torque spikes, the user may be notified that the jaws 410, 412 may not be fully closed, as at 1308. If the jaws 410, 412 are not fully closed, that may result in overstressing of grasped tissue or inadequate staple deployment. Once the user is notified, the user may have the option to proceed and finish the firing sequence, or reposition the end effector 404 to obtain a more suitable grasp of the tissue.

Algorithm for Optimizing Clamping

Figure 14:
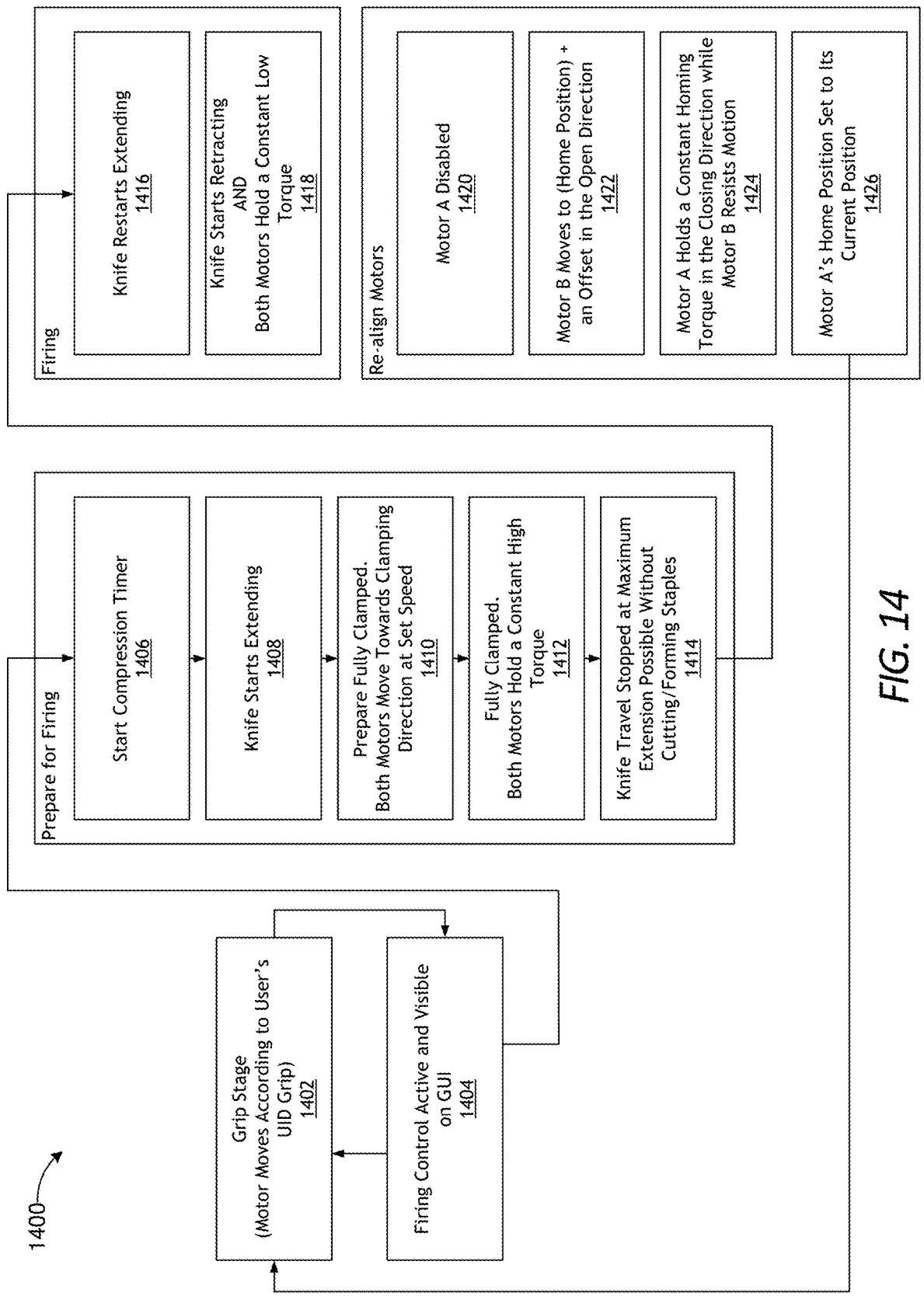
FIG. 14 is a schematic diagram of an example method of coordinating the clamping and firing functions of the surgical tool of FIG. 4.

FIG. 14 is a schematic diagram of an example method 1400 of coordinating the clamping and firing functions of the surgical tool 400 of FIG. 4, according to one or more embodiments. Before the surgical tool 400 can fire and thereby extend the knife 1202 (FIGS. 12A-12B) to cut tissue while simultaneously deploying staples to seal the tissue, the jaws 410, 412 (FIG. 4) must move through a gripping stage, where the jaws 410, 412 engage and start to grip the tissue, and a clamping (or compressing) stage, where the jaws 410, 412 clamp down on the grasped tissue. Accordingly, operation of the surgical tool 400 must transition from grasping tissue to clamping (compressing) the tissue to enable staple formation. The method 1400 may comprise an algorithm or software instructions that may be implemented (executed) by the computer system 606 of FIG. 6 to ensure that the clamping function coordinates properly with the firing sequence and the associated motion of the knife 1202.

As illustrated, the method 1400 may include entering the gripping stage, as at 1402. This occurs when a user manipulates the user input devices and sends a command signal interpreted by the computer system 606 (FIG. 6) to move the jaws 410, 412 (FIG. 4) to a particular orientation and start closing the jaws 410, 412. As indicated above, actuation of the jaws 410, 412 may be carried out by triggering operation of the motors 616 (FIG. 6) that operate the fourth and fifth drivers 610$d,e$ (FIG. 6) and thus cause operation of the closure cam gear 725 (FIGS. 7A-7B, 8, 9A-9B), which moves the closure tube 722 (FIGS. 7A-7B and 8) to open and close the jaws 410, 412. In some embodiments, once the jaws 410, 412 grip tissue at 90% capacity or more (and the tool has not already fired), the firing control may become active and visible on the visual display 206 (FIG. 2), as at 1404. If the firing control is not activated, the method 1400 returns to step 1402 to continue gripping until the 90% gripping capacity is reached or surpassed. Accordingly, full closure of the jaws 410, 412 and compression of grasped tissue only starts when the jaws 410, 412 are fully gripped (e.g., >90% capacity) and the firing control is activated.

If the firing control is activated, the method 1400 may proceed to prepare for firing by starting a compression timer, as at 1406. The compression timer tracks the time elapsed from when the jaws 410, 412 (FIG. 4) start clamping grasped tissue at full compression. This parameter will inform the user how far along the process is in the clamping stage. The knife 1202 (FIGS. 12A-12B) may then start extending, as at 1408, and the motors 616 (FIG. 6) that cause the jaws 410, 412 to clamp may be moved (rotated) towards the clamping direction at a set speed, as at 1410. If at least one of the motors 616 reaches or surpasses a predetermined torque limit indicating full clamping, the method 1400 may then proceed to hold the motors 616 at the constant high torque value, as at 1412.

According to one or more embodiments, the knife 1202 (FIGS. 12A-12B) may stop its distal movement at a maximum extension prior to cutting tissue and forming staples, as at 1414. In at least one embodiment, for example, the knife 1202 may stop at or near the point where the knife stop 1208 (FIG. 12B) comes into close contact with the jaw stop 1214 (FIG. 12B), but may alternately stop at another location. As will be appreciated, this can save time since the tissue needs to be compressed before fully firing, and compressing the tissue can take time. According to this step, the knife 1202 may be moved to a point just before firing occurs and may stay stationary at that point until the tissue is sufficiently compressed, at which point the knife 1202 can then be fired. Once the compression timer reaches a predetermined period for compressing the tissue, the knife 1202 may restart extension to cut the tissue and deploy the staples, as at 1416. Once reaching full extension after firing, the knife 1202 may start retracting by operating the motors 616 (FIG. 6) at a constant low torque, as at 1418, which helps in position control.

In some embodiments, the method 1400 may further include re-aligning the motors 616 (FIG. 6) used to close the jaws 410, 412 (FIG. 4). Upon retracting the knife 1202 (FIGS. 12A-12B), the computer system 606 (FIG. 6) changes control states on the closure mechanism from clamping (high torque) to position control (low or no torque). It is desired to re-align the motors angularly so that they can again be cooperatively used to manipulate the jaws 410, 412 as needed. To do this, one of the motors (Motor A) may be disabled, as at 1420, and the other motor (Motor B) may be moved to its home position, including a known offset in the open direction, as at 1422. As Motor B moves to the home position, Motor A holds a constant homing torque in the closing direction, which will be resisted by operation of Motor B, as at 1424. The home position for Motor A may then be set to the current position, as at 1426. This may be accomplished by changing the current position to a current position plus a pre-recorded offset in the opening direction, where the offset is a fraction of the expected mechanical backlash between Motor A and Motor B. Doing so sets the home position for Motor A within the backlash of Motor B, thereby preventing the motors A and B from counteracting each other when given simultaneous position commands.

Predict Stapling Force Using Position Dependent Efficiency Correction

During operation of the surgical tool 400 (FIG. 4), it may be desired or otherwise advantageous to determine the applied transection force caused by advancing the knife 1202 (FIGS. 12A-12B) to transect tissue grasped between the jaws 410, 412 (FIG. 4). Placing force sensors at the end effector 404 (FIG. 4), however, may be difficult. Instead, the torque sensors 628 (FIG. 6) and the rotary encoders 630 (FIG. 6) included in the drive housing 408 (FIG. 4) may be used to obtain torque and angular displacement measurements of the motor(s) 616 (FIG. 6) used to fire the knife 1202. The amount of force applied to the grasped tissue during transection can predict staple form outcomes. If the transection force is high, for instance, that may be an indication that the staples may not be formed accurately or properly, and the user may be advised that bleeding may occur following knife 1202 extension and once the jaws 410, 412 are subsequently opened.

As indicated above, one or more of the motors 616 (FIG. 6) may be actuated to rotate the sixth drive input 604f (FIG. 6), which correspondingly rotates the sixth drive shaft 702f (FIGS. 7A-7B) and an intermeshed drivetrain of gears used to cause the firing member 744 (FIGS. 7A-7B) to move. Lateral displacement of the firing member 744 causes corresponding lateral displacement of the firing rod 1206 (FIGS. 12A-12B) to advance and retract the knife 1202 (FIGS. 12A-12B), which transects tissue grasped between the jaws 410, 412 (FIG. 4) and simultaneously deploys staples to seal the cut tissue. The torque sensors 628 (FIG. 6) and the rotary encoders 630 (FIG. 6) may obtain real-time torque and angular displacement measurements of the motor 616 while actuating the sixth drive input 604f Using these measurements, in conjunction with the known mechanical advantage of the gearing drivetrain, would predict the transection force if the system were perfectly efficient. However, surgical tools, including the surgical tool 400 (FIG. 4), are not 100% efficient and depend heavily on the efficiency of the gearing mechanism used to drive the firing rod 1206, and the efficiency of the gears depends on gear angle, which is rarely precise. Moreover, the surgical tool 400 not only has inefficiencies, but these inefficiencies can also depend on the angular position of the motor 616, which dictates the state of the gearing drivetrain.

To accurately predict transection force, the efficiency of the surgical tool 400 (FIG. 4) during example operation may first be characterized. More specifically, the surgical tool 400 may be mounted to a "characterizer," which may comprise a laboratory test stand used to calibrate the surgical tool 400 prior to use. The characterizer is commonly a piece of equipment on the manufacturing line that can directly measure input torque and position as well as output force and position. With these measurements the efficiency of any individual device can be determined and recorded directly to that device's internal memory. Accordingly, the characterizer may be configured to measure the work output for a given motor 616 (FIG. 6) dedicated to firing the end effector 404 (FIG. 4) by measuring the force (torque) required by the motor 616 to fire the end effector 404 and a corresponding displacement of the knife 1202 (i.e., force×displacement/distance=work output). The characterizer may also be configured to measure and supply a work input, which may be determined from the torque assumed on the sixth drive input 604f (FIG. 6) to fire the end effector 404, and the angular displacement of sixth drive input 604f (i.e., torque×angle=work input). The torque and angular displacement may be measured for all angle ranges expected to be traversed (i.e., rotated through) during transection while firing the end effector 404. By dividing the work output by the work input, the efficiency of the mechanism used to fire the end effector 404 may then be calculated across the angle ranges expected to be traversed during transection.

Figure 15:
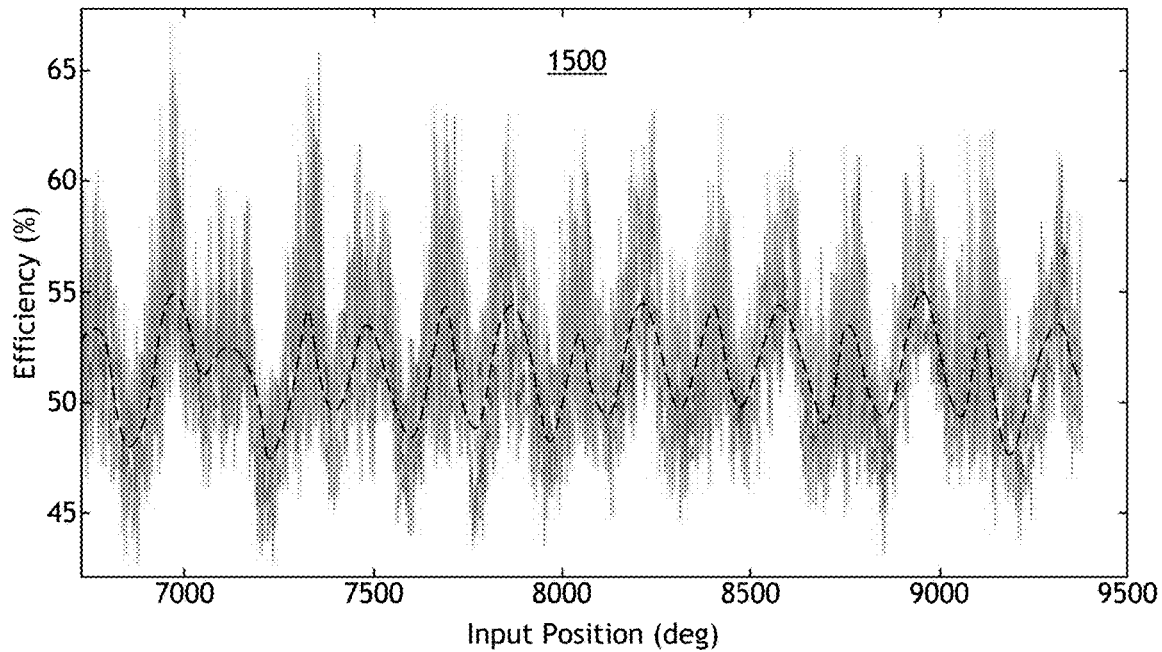
FIG. 15 is an example output plot derived from a characterizer used to measure efficiency of the surgical tool of FIG. 4 during operation.

FIG. 15 is an example output plot 1500 derived from a characterizer used to measure efficiency of the surgical tool 400 (FIG. 4) during operation. In the illustrated plot 1500, the effective efficiency (%) of a given motor and corresponding drivetrain ranges between about 45% and about 65% across input positions ranging between around 6500 degrees and 9500 degrees. As will be appreciated, and as illustrated, the efficiency percentage in the plot 1500 oscillates because it is tied to the manufacturing deviations in the gearing. Accordingly, the efficiency is linked to the angle of the drive input. Consequently, as the gearing drivetrain operates (rotates), the efficiency will change depending on what part of the gear is being used to transmit force. Using the plot 1500, for a given known angle of rotation of the motor, the efficiency will vary but may now be predictable.

The data derived in the plot 1500 may be populated into a lookup table and stored in memory on the surgical tool 400 (FIG. 4), such as in the memory 624 (FIG. 6) included in the internal computer 622 (FIG. 6). When the surgical tool 400 is placed in operation and the firing sequence is initiated for the end effector 404 (FIG. 4), the input torque and the angular displacement of the motor 616 (FIG. 6) may be measured, and the measured angle may be compared against the lookup table stored in the memory 624 to predict efficiency. The predicted efficiency may then be multiplied by the known input torque and the mechanical advantage of the drivetrain to calculate the actual transection force assumed at the end effector 404. In this embodiment, the mechanical advantage of the drivetrain pertains to gearing and actuation mechanisms for the firing system, which can be determined using kinematics based on the known gearing and gear ratios within the drivetrain.

Accordingly, while the efficiency of the gearing drivetrain may not be controlled, the efficiency can be characterized and stored in the memory 624 (FIG. 6) of the surgical tool 400 (FIG. 4). That characterization may then be queried in the form of the above-described lookup table to help correct the real-time torque reading measured on the motor 616 (FIG. 6). That torque measurement can be turned into a reliable force reading (output) at the knife 1202 (FIGS. 12A-12B), which then informs the user if staples are being formed through normal or difficult tissue. In one example, for instance, and with continued reference to the plot 1500 of FIG. 15, if the measured angular displacement is about 8000 degrees, that generally equates to an efficiency of about 50%. By combining the known mechanical advantage of the drivetrain with the measured input torque, and multiplying that result by a 50% efficiency value, it can be determined how much torque is actually being delivered to the grasped tissue at the jaws 410, 412.

In some embodiments, the predicted transection force can be compared to previous firings and communicated to the user (e.g., a surgeon) for an early warning of anomalous firings. More specifically, using the presently described method, the user may be informed before releasing the jaws 410, 412 (FIG. 4) after firing whether the staples were properly formed based on the amount of torque required to cut through the tissue. If the measured torque was above a predetermined limit, that may be an indication that the tissue being transected was more difficult (tough), which often results in improperly or inadequately deployed staples. Accordingly, this could be an early warning of anomalous tissue or that something went wrong during the firing sequence. In such instances, the user may be able to make intelligent decisions on next steps. In some embodiments, once it is determined that staples are being formed in difficult tissue, the user can stop the firing process and pull the knife 1202 (FIGS. 12A-12B) back before forming more staples. The user may then move to a different part (section) of the tissue to grasp and cut. Otherwise, the user may complete the transection with the understanding that there might be bleeding when they open the jaws 410, 412 (FIG. 4) resulting from poorly placed staples.

In another embodiment, torque feedback may be based on the corrected efficiency lookup table derived from the plot 1500. More particularly, a predetermined force (torque) limit may be programmed into the internal computer 622 (FIG. 6) of the surgical tool 400 (FIG. 4), and any measured torques above this limit would indicate that the end effector 404 (FIG. 4) may be attempting fire through difficult tissue and there is a possibility of generating improperly deployed staples. In such embodiments, the efficiency characterization may be queried to determine the tissue force and what torque is assumed on the motor 616 (FIG. 6) (accounting for device losses). The surgical tool 400 may then be programmed to operate the motor 616 in a way so that the torque/force is minimized.

While the foregoing examples described populating the efficiency lookup table with respect to the motor(s) 616 (FIG. 6) and associated gearing drivetrain used to fire the end effector 404 (FIG. 4), it will be appreciated that the foregoing principles may be equally applied to any of the motors 616 and corresponding gearing drivetrains used to operate any of the mechanical actuation functions of the surgical tool 400 (FIG. 4), without departing from the scope of the disclosure. Accordingly, similar efficiency correction could be applied to other systems, like the closure or wrist articulation systems of the surgical tool 400, to predict the clinical outcomes.

Pulsed Closure Control Methods

Because of the viscoelastic nature of tissue, it takes time and a high amount of force to fully clamp down on and compress tissue in preparation for firing. As described herein, the jaws 410, 412 (FIG. 4) of the surgical tool 400 (FIG. 4) can be opened and closed to clamp onto tissue by operating motors 616 (FIG. 6) configured to drive the fourth and fifth drivers 610*d,e* (FIG. 6), and driving the fourth and fifth drivers 610*d,e* correspondingly rotates the fourth and fifth drive inputs 608*d,e* (FIG. 6) and the interconnected fourth and fifth drive shafts 702*d,e* (FIGS. 7A-7B), respectively, to cause the pinions 724 (FIGS. 7A-7B, 8) attached to each drive shaft 702*d,e* to act on the closure cam gear 725 (FIG. 6). Rotating the closure cam gear 725 acts on the closure yoke 726 (FIGS. 7A-7B and 8), which causes the closure tube 722 (FIGS. 7A-7B, 8) to linearly displace and thereby open and close the jaws 410, 412 (FIG. 4). To obtain more clamping force that may help overcome and more effectively manage the viscoelasticity of clamped tissue, it is contemplated herein to pulse the application of force in closing the jaws 410, 412. A user may be able to accomplish this manually using repeated inputs provided through the user input devices. However, it may be beneficial to configure the surgical tool 400 to accomplish this autonomously, and thereby take advantage of the inertia of the closure cam gear 725, the intermeshed gear drivetrain, and the motor gear trains to drive the closure yoke 726 and interconnected closure tube 722 forward.

Figure 16A:
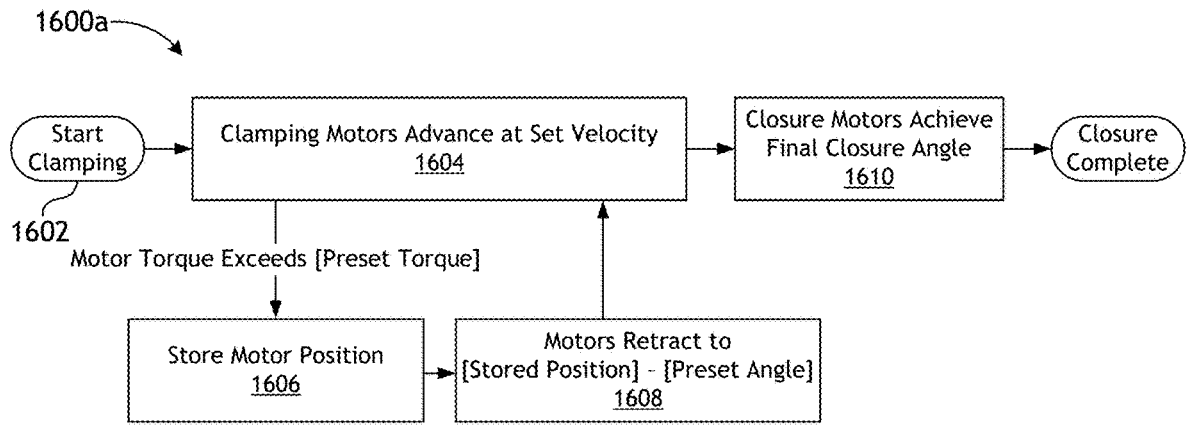
FIGS. 16A and 16B are schematic diagrams of example methods that accomplish pulsed closure control, according to one or more embodiments.
Figure 16B:
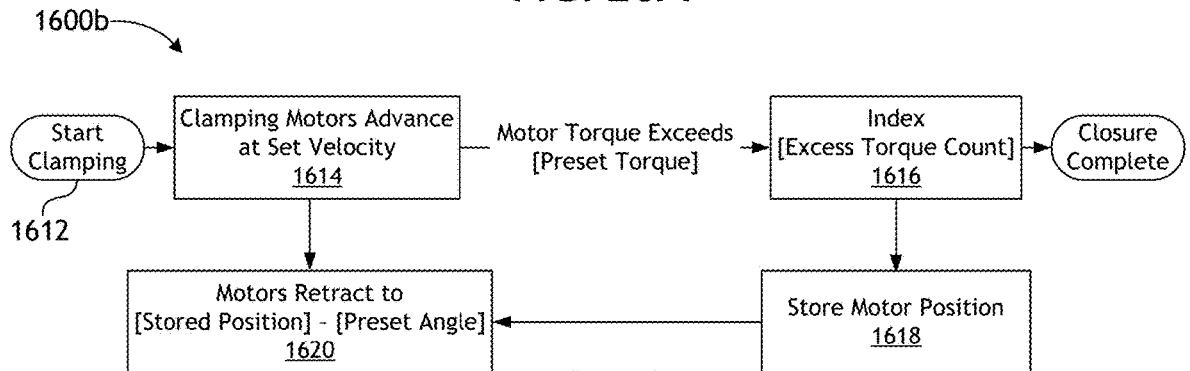

FIGS. 16A and 16B are schematic diagrams of example methods 1600*a* and 1600*b*, respectively, which accomplish pulsed closure control, according to one or more embodiments. The methods 1600*a,b* take advantage of the non-back drivable closure mechanism, including the closure cam gear 725 (FIGS. 8 and 9A-9B) and its cam profile 902 (FIGS. 9A-9B). More specifically, once the projection 802 (FIGS. 8 and 9A-9B) advances within the profile 902, the closure cam gear 725 is not naturally urged to unwind (i.e., reverse rotate), but instead tends to stay where it is. The benefit of this is that the motors 616 can be powered to advance the projection 802 within the profile 902, reverse the motors 616 a few degrees, and then power the motors 616 again to drive the projection 802 further within the profile 902. This pulsed motion of the motors 616 results in an increasing gripping force with each pulsed actuation. The methods 1600*a,b* may comprise algorithms or software instructions that may be implemented (executed) by the computer system 606 (FIG. 6) to control the motors 616 (FIG. 6) in a pulsed manner to achieve high clamping forces with minimum clamping mechanisms.

In FIG. 16A, the motors 616 (FIG. 6) are commanded to start the clamping process and thereby fully close the jaws 410, 412 (FIG. 4), as at 1602. The motors 616 may be commanded to operate at a constant (set) velocity for clamping, as at 1604. At some point, and depending on the thickness and viscoelasticity of the tissue being clamped, the constant velocity of the motors 616 cannot be maintained without exceeding a predetermined torque on the motors 616. The predetermined torque may comprise, for example, a preset torque value representative of a physical limit of the system, beyond which the motors 616 or the interconnected drivetrain of the closure mechanism might be overstressed or fail. If the measured torque on one or both of the motors 616 reaches the preset torque value, the angular position of the motors 616 is stored, as at 1606, at which point the motors 616 may be retracted (reversed) by a preset angular magnitude, as at 1608. The preset angular magnitude may be sufficient to move the motors 616 through the gearing backlash of the closure mechanism, but insufficiently to cause the jaws 410, 412 to commence re-opening.

The motors 616 may then be commanded to operate again at the constant velocity to continue clamping on the tissue, as at 1604. During this re-clamping process, the motors 616 move back through the gearing backlash at a high velocity because they are not operating against a tissue load, and the closure mechanism re-engages (e.g., slams into) the tissue at this high velocity, which helps compress the tissue quicker. This process is repeated until the motors 616 achieve a known final closure angle, as at 1610, at which point the jaws 410, 412 will be fully clamped.

In FIG. 16B, the motors 616 (FIG. 6) are commanded to start the clamping process and thereby fully close the jaws 410, 412 (FIG. 4), as at 1612. The motors 616 may be commanded to operate at a constant (set) velocity for clamping, as at 1614, and once the measured torque on one or both of the motors 616 exceeds a preset torque limit, an excess torque count will be indexed and recorded, as at 1616. If the excess torque count is less than a preset limit, the angular position of the motors 616 is stored, as at 1618, at which point the motors 616 may be retracted (reversed) by a preset angular magnitude, as at 1620. As with the method 1600a of FIG. 16A, the preset angular magnitude may be sufficient to move the motors 616 through the gearing backlash of the closure mechanism, but insufficiently to re-open the jaws 410, 412. The motors 616 may then be commanded to operate again at the constant velocity to continue clamping on the tissue, as at 1614. During this re-clamping process, the motors 616 move back through the gearing backlash at a high velocity and the closure mechanism re-engages the tissue at this high velocity, which helps compress the tissue quicker. Once the measured torque on the motors 616 exceeds the preset torque limit, another excess torque count will be indexed and recorded, as at 1616. This process is repeated until the excess torque count reaches a preset limit, at which point the jaws 410, 412 will be fully clamped.

In other embodiments, the motors 616 may be pulsed out of sequence. More particularly, the motors 616 may be retracted through the gearing backlash, following which the first motor 616 starts moving to clamp. When the first motor 616 has moved through a preset angular magnitude (distance), the second motor 616 may be commanded to start moving. Consequently, the first motor 616 hits the cam profile 902 (FIGS. 9A-9B) first and provides a first force pulse, and the second motor 616 hits the cam profile 902 shortly thereafter to provide a second force pulse. Consequently, the combined force pulse is wider but with a lower peak, but this may achieve a smoother pulsing effect with less harm to the reliability of the closure mechanism while maintaining a fast closure stroke.

FIG. 17 is a schematic side view of an example gear interface 1700 that may help pulse the closing force on the jaws 410, 412 (FIG. 4), according to one or more additional embodiments. More specifically, the closing force for closing the jaws 410, 412 (FIG. 4) may be pulsed by redesigning one or more of the gears of the drive train to obtain a larger backlash spacing. In at least one embodiment, the depicted drive gear may comprise one of the spur gears 724 (FIGS. 7A-7B and 8) and the depicted driven gear may comprise the closure cam gear 725 (FIGS. 7A-7B and 8). The gear interface 1700, however, may be representative of any of the drive and driven gears of the closure mechanism used to move the closure tube 722 (FIGS. 7A-7B and 8) to close the jaws 410, 412.

As illustrated, the teeth of the drive and driven gears may be intentionally segmented such that the spacing between opposing teeth is larger than normal. This creates a gap between tooth contact and a break in the rotation of the driven gear (e.g., the closure cam gear 725). The gap may be large enough to allow the motors 616 (FIG. 6) to increase velocity after each tooth has completed contact without the need to switch motor direction, and thereby pulse the closing force transmitted to the jaws 410, 412 (FIG. 4).

Correcting Clamping Effort (Force) Calculation for Closure Speed

As discussed above, it can be beneficial to measure the degree of clamping difficulty assumed by robotic surgical tools, such as the surgical tool 400 of FIG. 4 described herein, to inform the user (e.g., the surgeon, scrub nurse, etc.) whether staples may be properly formed or not upon firing the end effector 404 (FIG. 4). According to embodiments of this disclosure, the torque required to fully close the jaws 410, 412 may be corrected based on closure speed (i.e., angular velocity) of the motors 616 (FIG. 6) employed to operate the closure mechanism.

Because of the viscoelastic properties of tissue, the same piece of tissue can require more closure effort when clamped down on quickly as opposed to slowly. Correcting for the angular velocity (closure speed) of the motors 616 (FIG. 6) employed to operate the closure mechanism while closing the jaws 410, 412 (FIG. 4) can provide a more accurate indication of tissue properties. In one embodiment, the raw torque T, rotational angle Θ, and angular velocity ω values pertaining to the motor(s) 616 during a closure event on tissue may be recorded. Each value of the raw torque T may then be corrected in real-time using the recorded raw angular velocity ω and a pre-stored tissue damping property, which may be obtained during testing/characterization of the surgical tool 400 (FIG. 4). More specifically, the jaws 410, 412 may be grasp a reference material of a known area, and a known force may then be applied to the reference material. The displacement that the force induces on the tissue is then recorded as the tissue damping property. The corrected torque $T_{corrected}$ and the raw rotational angle Θ values may then be used to calculate the actual effort (force) required to fully clamp onto the tissue.

The following equation is one example correction equation that could be included in the control algorithm to calculate the actual effort (force) required to fully clamp onto the tissue:

$$T_{corrected} = \frac{T_{raw}}{(a*\omega^2 + b*\omega + c)}$$

where $T_{raw}$ is the raw torque measured at the motor(s) 616 (FIG), ω is the raw angular velocity of the motor(s) 616, and a, b, and c are constants related to tissue properties. More specifically, a is a constant representing the extra torque felt as a result of acceleration of the jaws 410, 412 (FIG. 4), b is a constant representing how much extra torque T is assumed at the motor(s) 616 (FIG. 6) due to the speed at which the tissue is being compressed, and c is the resistance torque that is constant at all speeds and acceleration (i.e., coulomb friction).

FIG. 18 depicts a torque T versus angle Θ plot 1802a juxtaposed with an angular velocity ω versus angle Θ plot 1802b. FIG. 18 also graphically depicts a corrected torque curve 1804 (shown as a dashed line) corresponding to $T_{corrected}$, which accounts for the dynamic properties of the tissue and thereby provides a more accurate measurement of the closure effort (force) required to fully clamp the jaws 410, 412 (FIG. 4). The torque curve 1806 in the upper plot 1802a and the angular velocity curve 1808 in the lower plot 1802b are the raw torque T and raw angular velocity ω, respectively, measured during an example clamping operation. As illustrated, the torque curve 1806 is defined by or otherwise includes a spike 1810 followed by a leveled out portion 1812. While applying a constant torque T during grasping, the spike 1810 in the torque curve 1806 occurs, and by referencing the angular velocity curve 1808, additional insight can be obtained. More particularly, it can be seen that the torque spike 1810 resulted in a corresponding spike 1814 in the angular velocity curve 1808. By applying the above-described correction factor, the corrected torque curve 1804 at that location indicates that the spike 1810 was a result of the speed, not that the tissue was actually difficult to clamp. Said differently, if the user had grasped on the tissue with a slower speed in the same region, there would not have been a spike 1810.

At a point later in the clamping process, the torque T remains flat across the leveled out portion 1812, but the angular velocity ω dips significantly while at the same rotational angle Θ. The corrected torque 1804 shows that the torque T actually increased across the rotational angle Θ, which could be an indication that the jaws 410, 412 (FIG. 4) may be clamping on tougher tissue.

Final Clamping Angle Comparison Indicates Clamping Effort (Force)

As discussed above, it can be beneficial to measure the degree of clamping difficulty assumed by robotic surgical tools, such as the surgical tool 400 of FIG. 4 described herein, to inform the user (e.g., the surgeon, scrub nurse, etc.) whether staples may be properly formed or not upon firing the end effector 404 (FIG. 4). According to embodiments of this disclosure, the extension of the clamping (closure) mechanism under load may be used to help indicate clamping effort and/or difficulty to the user. More specifically, the maximum achieved rotational angle of the motor(s) 616 (FIG. 6) used to facilitate closure of the jaws 410, 412 (FIG. 4) will decrease as the thickness of grasped tissue increases, which may prove advantageous in providing an inverse relationship between final closure angle and closure effort.

In one or more embodiments, the surgical tool 400 (FIG. 4) may first be characterized during manufacturing. More particularly, a low torque reference closure angle for the motor(s) 616 (FIG. 6) may be determined by applying a low closure motor torque and fully closing the jaws 410, 412 (FIG. 4). The maximum motor angle achieved at closing comprises the low torque reference closure angle. The jaws 410, 412 may then be clamped at full closure torque while measuring the rotational angle of the motor(s) 616 to obtain a high torque reference closure angle. The jaws 410, 412 may then be clamped on a thick reference material at full closure torque while measuring the rotational angle of the motor(s) 616 to obtain a working closure angle. The thick reference material substantially mimics tissue and may comprise, for example, fixed durometer rubber or foam. The low and high torque reference closure angles and the working closure angle may then be stored in the surgical tool 400, such as in the memory 624 (FIG. 6) of the internal computer 622 (FIG. 6)

In example operation, the rotational angle of the motor(s) 616 (FIG. 6) used to facilitate closure of the jaws 410, 412 (FIG. 4) may be tracked (measured) while clamping on tissue. The distance of the measured rotational angle of the motor(s) 616 to home while clamped on the tissue may be compared against the low and high torque reference closure angles and the working closure angle stored in the surgical tool 400. The user (e.g., a surgeon, scrub nurse, etc.) may then be notified of the comparison and thereby determine if the jaws 410, 412 are clamping with relatively low or high effort (force), and can decide if the effort is expected given the observed tissue environment.

In one or more additional embodiments, the effort (force) required to fully clamp the jaws 410, 412 (FIG. 4) may be calculated from the area under two or more torque T vs. rotational angle Θ curves. More specifically, FIG. 19 depicts a first torque-angle curve 1902a juxtaposed with a second torque-angle curve 1902b. The first torque-angle curve 1902a may be plotted and stored during manufacturing (calibration) of the surgical tool 400 (FIG. 4) by clamping down on a thick reference material, and the second torque-angle curve 1902b may be plotted and stored during manufacturing by clamping down on a thin reference material. A third torque-angle curve 1904 may be plotted during real-time use of the surgical tool 400 while clamping on tissue with the jaws 410, 412. By characterizing the bounds of the first and second curves 1902a,b, it may be possible to monitor the measured clamping forces of the third curve 1904 during operation and indicate to the user how close the real-time clamping force is to the first or second curves 1902a,b, and thereby inform the user whether thick or thin tissue is being clamped.

Indication of how close the measured clamping forces 1904 are to the first or second curves 1902a,b may be determined by calculating the area under the torque-angle curve 1904 measured during closure, and comparing that measurement to the area under the reference torque-angle curves 1902a,b initially characterized during manufacturing. In FIG. 19, i represents each point of the measured curve 1904 along the rotational angle Θ. Consequently, if data is captured at 1,000 angles Θ, i would be 1,000. Calculating the effort (force) can be determined using the following pseudo-code, executable by the computer system 606 of FIG. 6:

```
thick_count = 0
thin_count = 0
for i = 1 to length (Θ)
    if (T_thick[i] - T_measured[i]) < (T_measured[i] - T_thin[i])
        thick_count ++
    else
        thin_count --
```

In the above pseudo-code, $T_{thick}[i]$ is the $i^{th}$ value on the thick reference curve 1902a, $T_{thin}[i]$ is the $i^{th}$ value on the thin reference curve 1902b, and $T_{measured}[i]$ is the $i^{th}$ value on the real-time measured curve 1904. Accordingly, the distance between $T_{thick}$ and $T_{measured}$ is calculated at and if that is less than the difference between $T_{measured}$ and $T_{thin}$, then a point (index value) is added to the thick_count, but if $T_{measured}$ is closer to $T_{thin}$, then a point (index value) is added to the thin_count. This calculation is made at all rotational angles Θ for $T_{measured}$ and final tally of thick_count and thin_count may be indicative of whether the jaws 410, 412 (FIG. 4) are clamping on thick or thin tissue. This result may be provided to the user, such as in the form of a ratio, to allow the user to consider whether firing the end effector 404 (FIG. 4) is advisable or not.

Embodiments disclosed herein include:

A. A surgical tool that includes a drive housing, a closure tube that extends from the drive housing, an end effector arranged at an end of the closure tube and having opposing jaws, a closure yoke mounted to the closure tube and having a projection extending therefrom, and a gearing assembly including one or more spur gears attached to a corresponding one or more drive shafts such that rotation of the one or more drive shafts correspondingly rotates the one or more spur gears, and a closure cam gear positioned to intermesh with the one or more spur gears and defining a profile that receives the projection, wherein rotating the one or more spur gears causes the closure cam gear to rotate, which causes the projection to traverse the profile, and wherein traversing the profile with the projection urges the closure yoke and the closure tube to linearly displace and thereby actuate the jaws.

B. A method of operating a surgical tool, the surgical tool having a drive housing, a closure tube extending from the drive housing, an end effector arranged at an end of the closure tube and having opposing jaws, and a closure yoke mounted to the closure tube and having a projection extending therefrom, the method including mounting the drive housing to a tool driver of a robotic surgical system, actuating one or more motors of the tool driver to actuate a gearing assembly that includes one or more spur gears attached to a corresponding one or more drive shafts such that rotation of the one or more drive shafts correspondingly rotates the one or more spur gears, and a closure cam gear positioned to intermesh with the one or more spur gears and defining a profile that receives the projection. The method further including rotating the one or more spur gears to rotate the closure cam gear and thereby causing the projection to traverse the profile, and urging the closure yoke and the closure tube to linearly displace as the projection traverses the profile and thereby actuating the jaws.

Each of embodiments A and B may have one or more of the following additional elements in any combination: Element 1: wherein the profile comprises a slot in the shape of a spiral. Element 2: wherein the profile provides first and second ends and extends between the first and second ends at a constantly changing radius. Element 3: wherein the profile provides first and second ends and extends between the first and second ends at two or more constant slopes. Element 4: wherein the profile provides a first arcuate region extending from the first end at a first constant slope and a second arcuate region extending from the first arcuate region at a second constant slope toward the second end, and wherein the first and second constant slopes are different. Element 5: wherein the first arcuate region provides a first mechanical advantage to the gearing assembly and the second arcuate region provides a second mechanical advantage to the gearing assembly, and wherein the second mechanical advantage is greater than the first mechanical advantage. Element 6: wherein, as the projection traverses the first arcuate region, the linear displacement of the closure yoke and the closure tube is faster but with less output force as compared to when the projection traverses the second arcuate region. Element 7: wherein the profile provides at least one straight region. Element 8: wherein the gearing assembly further includes a control tool accessible to a user, a drive gear positioned on an underside of the control tool, and a driven gear attached to the closure cam gear and positioned to intermesh with the drive gear, wherein manual rotation of the control tool correspondingly rotates the closure cam gear and causes the projection to traverse the profile.

Element 9: wherein the profile provides first and second ends and extends between the first and second ends at a constantly changing radius, the method further comprising providing a constant mechanical advantage to the gearing assembly as the projection traverses the profile. Element 10: wherein the profile provides first and second ends, a first arcuate region extending from the first end at a first constant slope, and a second arcuate region extending from the first arcuate region at a second constant slope different from the first constant slope and toward the second end, the method further comprising providing a first mechanical advantage to the gearing assembly as the projection traverses the first arcuate region, and providing a second mechanical advantage to the gearing assembly as the projection traverses the second arcuate region, wherein the second mechanical advantage is greater than the first mechanical advantage. Element 11: further comprising moving the jaws to a closed position as the projection traverses the first arcuate region, and clamping on tissue with the jaws as the projection traverses the second arcuate region. Element 12: wherein the profile provides at least one straight region. Element 13: wherein the gearing assembly further includes a control tool accessible to a user, a drive gear positioned on an underside of the control tool, and a driven gear attached to the closure cam gear and positioned to intermesh with the drive gear, the method further comprising manually rotating the control tool and thereby rotating the closure cam gear to cause the projection to traverse the profile and actuate the jaws.

By way of non-limiting example, exemplary combinations applicable to A and B include: Element 3 with Element 4; Element 4 with Element 5; Element 5 with Element 6; Element 3 with Element 7; Element 10 with Element 11; and Element 10 with Element 12.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
    a drive housing;
    a closure tube that extends from the drive housing;
    an end effector arranged at an end of the closure tube and having opposing jaws;
    a closure yoke rotationally mounted but axially fixed to the closure tube and having a projection extending therefrom; and
    a gearing assembly including:
        one or more spur gears attached to a corresponding one or more drive shafts such that rotation of the one or more drive shafts correspondingly rotates the one or more spur gears; and
        a closure cam gear positioned to intermesh with the one or more spur gears and defining a profile that receives the projection, the closure cam gear being rotatably mounted to the closure yoke at the projection,
    wherein rotating the one or more spur gears causes the closure cam gear to rotate, which causes the projection to traverse the profile, and
    wherein traversing the profile with the projection urges the closure yoke and the closure tube to linearly displace and thereby actuate the opposing jaws.

2. The surgical tool of claim 1, wherein the profile comprises a slot in the shape of a spiral.

3. The surgical tool of claim 1, wherein the profile provides first and second ends and extends between the first and second ends at a constantly changing radius.

4. The surgical tool of claim 1, wherein the profile provides first and second ends and extends between the first and second ends at two or more constant slopes.

5. The surgical tool of claim 4, wherein the profile provides a first arcuate region extending from the first end at a first constant slope and a second arcuate region extending from the first arcuate region at a second constant slope toward the second end, and wherein the first and second constant slopes are different.

6. The surgical tool of claim 5, wherein the first arcuate region provides a first mechanical advantage to the gearing assembly and the second arcuate region provides a second mechanical advantage to the gearing assembly, and wherein the second mechanical advantage is greater than the first mechanical advantage.

7. The surgical tool of claim 6, wherein, as the projection traverses the first arcuate region, the linear displacement of the closure yoke and the closure tube is faster but with less output force as compared to when the projection traverses the second arcuate region.

8. The surgical tool of claim 4, wherein the profile provides at least one straight region.

9. The surgical tool of claim 1, wherein the gearing assembly further includes:
    a control tool accessible to a user;
    a drive gear positioned on an underside of the control tool; and
    a driven gear attached to the closure cam gear and positioned to intermesh with the drive gear,
    wherein manual rotation of the control tool correspondingly rotates the closure cam gear and causes the projection to traverse the profile.

10. A method of operating a surgical tool, the surgical tool having a drive housing, a closure tube extending from the drive housing, an end effector arranged at an end of the closure tube and having opposing jaws, and a closure yoke rotationally mounted but axially fixed to the closure tube and having a projection extending therefrom, the method comprising:
    mounting the drive housing to a tool driver of a robotic surgical system;
    actuating one or more motors of the tool driver to actuate a gearing assembly that includes:
        one or more spur gears attached to a corresponding one or more drive shafts such that rotation of the one or more drive shafts correspondingly rotates the one or more spur gears; and
        a closure cam gear positioned to intermesh with the one or more spur gears and defining a profile that receives the projection, the closure cam gear being rotatably mounted to the closure yoke at the projection;
    rotating the one or more spur gears to rotate the closure cam gear and thereby causing the projection to traverse the profile; and
    urging the closure yoke and the closure tube to linearly displace as the projection traverses the profile and thereby actuating the jaws.

11. The method of claim 10, wherein the profile provides first and second ends and extends between the first and second ends at a constantly changing radius, the method further comprising providing a constant mechanical advantage to the gearing assembly as the projection traverses the profile.

12. The method of claim 10, wherein the profile provides first and second ends, a first arcuate region extending from the first end at a first constant slope, and a second arcuate region extending from the first arcuate region at a second constant slope different from the first constant slope and toward the second end, the method further comprising:
    providing a first mechanical advantage to the gearing assembly as the projection traverses the first arcuate region; and
    providing a second mechanical advantage to the gearing assembly as the projection traverses the second arcuate region, wherein the second mechanical advantage is greater than the first mechanical advantage.

13. The method of claim 12, further comprising:
    moving the jaws to a closed position as the projection traverses the first arcuate region; and
    clamping on tissue with the jaws as the projection traverses the second arcuate region.

14. The method of claim 12, wherein the profile provides at least one straight region.

15. The method of claim 10, wherein the gearing assembly further includes a control tool accessible to a user, a drive gear positioned on an underside of the control tool, and a driven gear attached to the closure cam gear and positioned to intermesh with the drive gear, the method further comprising:
   manually rotating the control tool and thereby rotating the closure cam gear to cause the projection to traverse the profile and actuate the jaws.

* * * * *